(12) United States Patent
Ishikawa et al.

(10) Patent No.: US 7,002,145 B2
(45) Date of Patent: Feb. 21, 2006

(54) DETECTION METHOD AND DETECTION DEVICE OF SPECIAL DRUGS

(75) Inventors: Masaki Ishikawa, Tokyo (JP); Masaki Matsumoto, Hitachinaka (JP); Yoshihiro Nishikawa, Hitachi (JP); Yasuaki Takada, Kiyose (JP); Hisashi Nagano, Hachioji (JP); Masami Sakamoto, Hitachinaka (JP)

(73) Assignees: Hitachi, Ltd., Tokyo (JP); Hitachi High-Technologies Corporation, Tokyo (JP)

( * ) Notice: Subject to any disclaimer, the term of this patent is extended or adjusted under 35 U.S.C. 154(b) by 8 days.

(21) Appl. No.: 10/756,458

(22) Filed: Jan. 14, 2004

(65) Prior Publication Data

US 2004/0195499 A1 Oct. 7, 2004

(30) Foreign Application Priority Data

Mar. 31, 2003 (JP) .............................. 2003-096487

(51) Int. Cl.
*H01J 49/42* (2006.01)
(52) U.S. Cl. ................................... 250/288
(58) Field of Classification Search ................ 250/288, 250/281, 282; 280/282
See application file for complete search history.

(56) References Cited

U.S. PATENT DOCUMENTS

| 5,092,155 A | 3/1992 | Rounbehler et al. |
|---|---|---|
| 5,181,427 A | 1/1993 | Elias et al. |
| 5,425,263 A | 6/1995 | Davies et al. |
| 5,741,984 A | 4/1998 | Danylewych-May et al. |
| 6,610,977 B1 * | 8/2003 | Megerle ..................... 250/287 |
| 6,649,910 B1 * | 11/2003 | Sakairi ....................... 250/288 |
| 6,884,997 B1 * | 4/2005 | Kashima et al. ............ 250/288 |
| 6,894,276 B1 * | 5/2005 | Takada et al. .............. 250/292 |

FOREIGN PATENT DOCUMENTS

| EP | 0447158 | 3/1991 |
|---|---|---|
| GB | 2363517 | 12/2001 |
| JP | 2-296128 | 12/1990 |
| JP | 5-332894 | 12/1993 |
| JP | 7-85834 | 3/1995 |
| JP | 7-134970 | 5/1995 |
| JP | 2001-93461 | 4/2001 |
| WO | WO02/25265 | 3/2002 |

* cited by examiner

*Primary Examiner*—Kiet T. Nguyen
(74) *Attorney, Agent, or Firm*—Mattingly, Stanger, Malur & Brundidge, P.C.

(57) ABSTRACT

Firstly, the following check chip is set up into a heater: A check chip onto which a sample has been picked up by wiping out the surface of a check target, or a check chip formed by absorbing and collecting the sample into a filter. Here, the filter has been set up in a vibration-type or heating-type portable-type absorption probe in an attachment/detachment-capable manner. Secondly, a sample gas generated from the heated check chip is analyzed using a tandem-type mass spectrometer. This makes it possible to simplify the sample pick-up from various types of check targets, and to shorten the pick-up time and the checking time.

3 Claims, 17 Drawing Sheets

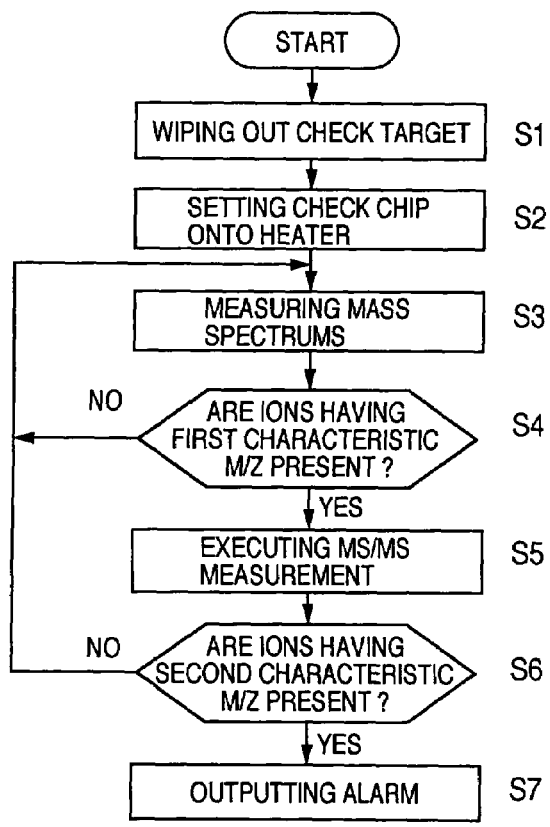
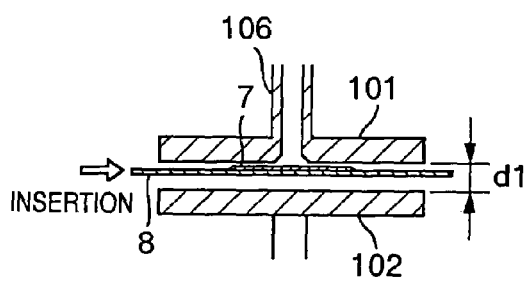
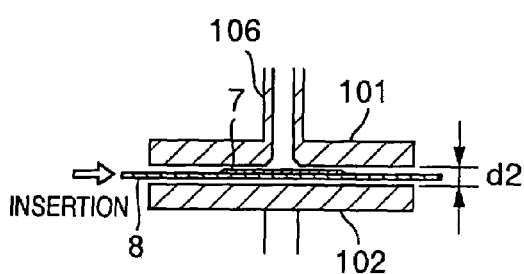

DETECTION METHOD AND DETECTION DEVICE OF SPECIAL DRUGS

BACKGROUND OF THE INVENTION

1. Field of the Invention

The present invention relates to detection technologies for gunpowder-kind materials such as explosive substances, dangerous objects such as flammable substances, poisonous gases, and legally prohibited medications such as drugs (all of which, hereinafter, will be generically referred to as "special drugs" for convenience). More particularly, it relates to a detection method and its device that, by using a mass spectrometer, detect whether or not a special drug is present inside, e.g., baggage such as a piece of hand baggage, freight, and a suspicious object.

2. Description of the Related Art

Generally speaking, in such locations as an airport and an event grounds where a large number of people come and gather, a detection device has become necessary which is designed for detecting special drugs such as an explosive substance. This detection device is requested for implementing the safety of passengers and event participants, or the maintenance of public peace and order there. Moreover, a request for a detection device has been also made for checking a suspicious object in, e.g., a mail, a home-delivered parcel, and a rental safe-deposit box of a bank. As one of the detection devices of this kind, a hand-baggage checking device using an X-ray transmittance device, a metal detector, or the like has been widely used with airports as its center. Here, the X-ray detection device or the like is based on a detection scheme referred to as "bulk detection". In the bulk detection, a special drug to be detected as a target is recognized as a piece of lump, then judging the presence based on information about its configuration or the like. Also, a detection method on the basis of gas analyses is referred to as "trace detection", where a substance is identified from the chemical analysis information. The trace detection exhibits a characteristic of making it possible to detect the extremely small amounts of components adhering to a bag or the like. In particular, in accompaniment with a tendency to seek security enhancements socially, a device is now desired which, by a combination of the bulk detection and the trace detection, allows a dangerous object to be detected with a higher accuracy.

Meanwhile, in order to find out legally prohibited drugs brought in via various routes, the detection device is also used at a customhouse or the like. Although, at the customhouse, the bulk detection device and drug detection dogs are mainly used, it is now being requested to implement a trace analysis device designed for the legally prohibited drugs in substitution for the drug detection dogs. In the trace detection, the various analysis methods, such as the ion mobility spectroscopy and the gas chromatography, are being attempted. In addition, the development and research of a device which simultaneously exhibits all of the following characteristics is now being promoted: The detection speed and sensitivity to be requested as the detection device, and the selectivity of making it possible to detect a specific substance in a selective manner.

In the situation like this, since, basically, the mass spectroscopy is superior in the detection speed, the sensitivity, and the selectivity, a detection technology on the basis of the mass spectroscopy has been proposed (refer to JP-A-7-134970). According to this technology, the presence or absence of a special drug is judged as follows: A sample gas is absorbed by an absorption probe, thereby being guided into an ion-source so as to be ionized. Next, the ions of the sample gas containing drugs are converged by being passed through an electrostatic lens or the like, then being guided into a detector to measure the mass spectrums of the sample gas. Moreover, based on this measurement result, a data processing unit including a computer or the like identifies one or plural m/z (i.e., ion mass-number/ion charge-number) value or values indicating a special drug or drugs, thereby creating the mass spectrum or spectrums. Furthermore, the presence or absence of the special drug is judged based on this mass spectrum, and also its type is identified at the same time. Finally, if the special drug has been detected, an alarm or the like is outputted to be displayed.

However, here, there exists a case where a chemical substance, from which ions having the same m/z value as that of ions generated from a special drug will be generated, is present in the sample gas. In this case, there exists a possibility of issuing a false report, i.e., the alarm is displayed despite the fact that no special drug is present. For example, there has existed a possibility that, at the time of detecting a stimulant inside a piece of hand baggage, a false report is issued in reaction to a component of cosmetics put inside the hand baggage. This phenomenon, which is attributed to the low selectivity of a mass analysis unit for analyzing ions, is caused by its inability to distinguish between ions resulting from the stimulant and ions resulting from the cosmetics both of which have the same m/z value by chance.

As a method of enhancing the selectivity in the mass analysis like this, the tandem mass spectroscopy has been proposed. In the tandem mass spectroscopy, the mass analysis is performed at two stages, using a triplet quadrupole mass spectrometer or a quadrupole ion-trap mass spectrometer. Namely, in the mass analysis at a first stage, the m/z values of the ions generated at the ion-source are measured. Next, from among the ions having the various m/z values, ions having a specific m/z value are selected. Moreover, the selected ions (i.e., precursor ions) are dissociated by the collision with a neutral gas or the like, thereby generating decomposition ions (i.e., fragment ions). Furthermore, in the mass analysis at a second stage, the mass analysis of the fragment ions is performed. In the tandem mass spectroscopy like this, when any one of the precursor ions is dissociated, which of the sections within its molecule will be cut off depends on the chemical-bond strength on each section basis. Consequently, analyzing the fragment ions allows the acquisition of the mass spectrums which include exceedingly ample information about the molecular structures of the precursor ions. As a result, even if the m/z values of the ions generated at the ion-source are identical to each other by chance, by checking the mass spectrums of the fragment ions, it becomes possible to judge whether or not the special drug to be detected is contained in the sample gas.

The tandem mass spectroscopy, however, necessitates a longer checking time as compared with the normal mass spectroscopy. This condition results in, e.g., an undesirable possibility of causing a traffic congestion of plural pieces of hand baggage flowing on board a hand-baggage transportation bench. Accordingly, in order to shorten the checking time needed for the tandem mass spectroscopy, the following proposal has been made (refer to W0-02/25265A1): Namely, only when the precursor ions resulting from the special drug have been detected in the mass analysis at the first stage, the mass analysis at the second stage is executed. This proposal is based on an assumption that no special drug is contained in almost all the pieces of hand baggage.

In this way, it is possible to shorten the time needed for the mass analysis of the special drug. Nevertheless, this checking method still necessitates too much time because of its checking way, i.e., in the hand-baggage checking or the like, trouble is taken to open suitcases, briefcases, bags, parcels, and the like one by one, and the air around goods stored inside the hand baggage is absorbed. Accordingly, the following attempt has been made (refer to JP-A-7-134970): Namely, the sample gas leaking from a piece of hand baggage or the like is absorbed by the absorption probe or the like, thereby being introduced into the mass spectrometer via a pipe path such as a hose. However, there exist occasions where, depending on the type and packing style of the special drug, the special drug leaking from the baggage or the like is too small in amount, or the special drug is the type of special drug that is difficult to become the gas (i.e., vapors) at the room temperature. On these occasions, merely absorbing the air on the surface of the check target by the absorption probe, in some cases, gives rise to a problem that the sample gas introduced into the mass spectrometer is insufficient in amount or concentration. Also, if the check target on the check bench and the mass spectrometer are positioned with a considerable distance apart, it takes the sample gas a time to reach the ion-source via the pipe path such as the hose. This results in a problem that the detection speed is lowered.

As a countermeasure hereto, conventionally, portable-type sample pick-up devices have been proposed (refer to JP-A-5-332894 and JP-A-2-296128). The sample pick-up device disclosed in JP-A-5-332894 is as follows: A sample-collecting filter is inserted into a casing with a built-in absorption fan such that the sample-collecting filter is in an attachment/detachment-capable manner into/from the front-end portion of an absorption pipe. This configuration collects environmental-pollution substances and dangerous objects existing in the air. Also, according to JP-A-2-296128, the sample pick-up device heats the surface of the check target to vaporize substances adhering to the surface. Simultaneously, the device intermittently injects an air-jet to promote the removal of the substances adhering to the surface, then absorbing the vaporized sample from the aperture of a nozzle so as to capture the sample into a collector. This collector, which includes a metallic ribbon wound in a coil-shaped manner inside a cylinder-shaped housing, allows the sample gas to be captured on the surface of the metallic ribbon by adsorption or the like. Concerning the sample captured into the collector, after the nozzle of the sample pick-up device has been connected to a sample absorption opening of the mass spectrometer, the collector is heated so as to detach the adsorbed sample. This makes it possible to introduce the sufficient amount and concentration of sample gas into the mass spectrometer.

By the way, the portable-type sample pick-up devices disclosed in JP-A-5-332894 and JP-A-2-296128 allow the detection by the mass spectrometer to be easily performed even if the check target is a freight container, a vehicle, or the like which is located outdoors.

Nevertheless, the sample pick-up device disclosed in JP-A-5-332894 has the following problem: Namely, on the occasions where the special drug leaking from the baggage or the like is too small in amount, or the special drug is the type of special drug that is difficult to become the gas (i.e., vapors) at the room temperature, merely absorbing the air on the surface of the check target by the absorption fan, in some cases, gives rise to a problem that the picked-up sample is insufficient in amount or concentration. Meanwhile, the sample pick-up device disclosed in JP-A-2-296128 has the following problem: Namely, if, when performing the checking continuously, a sample at a preceding checking remains on the collector without being fully vaporized, the reliability of the subsequent checking is lowered. This is because the collector for capturing the sample is integrally molded with the main body of the pick-up device. When trying to solve the problem like this, treatments such as washing the collector and its periphery must be performed. This results in a problem that the checking speed cannot be increased. Also, if there exist the large number of check targets, the sample pick-up devices corresponding to the number of the check targets must be prepared, which is inconvenient.

SUMMARY OF THE INVENTION

It is a first object of the present invention to provide a special drug detection method and its device that allow a sample pick-up to be easily performed from various types of check targets, and that make it possible to shorten the pick-up time and the checking time.

Also, it is a second object of the present invention to provide a special drug pick-up device that allows a sample pick-up to be easily performed from various types of check targets, and that makes it possible to shorten the pick-up time and the checking time.

A sample pick-up method of the present invention is as follows: Using a check chip such as a piece of paper, a piece of cloth, or a piece of filter paper (i.e., filter), the surface or the like of a check target is wiped out, thereby picking up a sample on the check chip. Otherwise, the check chip such as the filter is provided on an absorption-flow path of a portable-type absorption probe in an attachment/detachment-capable manner into/from the absorption-flow path, and the air on the surface of or in the proximity to the check target is absorbed by this absorption probe so as to pick up the sample on the check chip. Next, the check chip to which the picked-up sample adheres is heated so as to vaporize the sample, thereby introducing the sample gas into a mass spectrometer.

According to this method, the wipe-out operation of the check-target surface is performed or, the air on the surface of or in the proximity to the check target is absorbed by the portable-type absorption probe, thereby making it possible to collect the sample on the check chip. This characteristic, accordingly, allows the sample to be easily picked up even if the check target is a freight container, a vehicle, or the like which is located outdoors. Also, since the check chip is inexpensive, preparing the large number of check chips allows samples to be picked up from a large number of check targets at the same time. Also, the check chip is heated so as to generate the sample gas, thereby making it possible to easily introduce the sample into the mass spectrometer. This characteristic shortens a time needed from the sample pick-up to the sample introduction into the mass spectrometer, thereby making it possible to shorten the detection time in total.

Also, a special drug detection method of the present invention includes the following steps: A step of heating a check chip to which a sample picked up from a check target adheres, a step of absorbing, as a sample gas, a gas generated from the heated check chip, a step of ionizing the absorbed sample gas, a first analysis step of analyzing masses of ions of the ionized sample gas thereby to acquire mass spectrums thereof, a first judgment step of judging whether or not ions having a first characteristic m/z value are present on the basis of the mass spectrums acquired at the first analysis step, a second analysis step of performing a tandem mass spectrometry in correspondence with a judgment result acquired at the first judgment step, and a second judgment step of judging whether or not ions having a second characteristic m/z value are present on the basis of mass spectrums acquired by the tandem mass spectrometry.

In this case, it is preferable that this method further include a step of outputting a judgment result in correspondence therewith, the judgment result being acquired at the second judgment step. This judgment-result outputting step can be embodied as a notification step of issuing an alarm.

Also, the step of heating the check chip can be embodied as a step of heating the check chip in a state of being introduced into a vaporization unit. Then, by absorbing the surrounding air as a carrier gas from the vaporization unit, the sample gas generated from the heated check chip can be guided to the first analysis step. It is desirable that the vaporization unit in this case include two sheets of heating plates which are opposedly located with a certain spacing apart, and that the check chip be heated in a state of being inserted between the two sheets of heating plates.

Incidentally, in substitution for the above-described mass analysis steps, the publicly known methods are applicable. For example, the following steps can configure the mass analysis steps: The step of analyzing masses of ions of the ionized sample gas so as to acquire mass spectrums thereof, the step of judging the presence or absence of ions having a specific m/z value on the basis of the acquired mass spectrums, and the step of outputting the judgment result.

Also, a special drug sample pick-up device of the present invention includes the following configuration components: A case for storing an absorption fan, a driving source for driving the absorption fan, and a power-supply, an absorption nozzle mounted forward of the case and including therein a sample pick-up unit of vibration, air-injection, or heating, and a sample pick-up filter. Here, the sample pick-up filter is located between the case and the absorption nozzle in an insertion/extraction-capable manner, and a sample absorbed by the absorption nozzle adheres to the sample pick-up filter.

In this case, a set-up unit of the filter is provided on a connection unit between the absorption nozzle and the case. The filter is configured to include a grasp unit which is provided at a circumferential edge of a ring-shaped frame of the filter. Here, an aperture portion positioned at the inner side of the frame is formed in a manner of being decentered in a direction moving away from the grasp unit. The filter is set up in such a manner that this aperture portion will be filled. Also, in the filter set-up unit, a slit whose width is equal to the thickness of the filter is formed along a half circumference of the outer circumferential wall of the absorption nozzle. The filter is formed in an insertion/extraction-capable manner into/from this slit.

Also, in substitution for the method of heating the check chip with which the surface of the check target has been wiped out, or the check chip such as the filter on which the sample has been picked up by the portable-type absorption probe, the absorption probe can directly be communicated to the ion-source of the mass spectrometer. In this case, a vibration is applied to the check target, thereby making it possible to absorb, as the sample gas, the air on the surface of or in the proximity to the check target. This can be embodied by providing a vibration applier for applying the vibration to the check target, and the absorption probe for absorbing, as the sample gas, the surrounding air on the surface of or in the proximity to the check target. Here, the vibration applier may apply the vibration to a transportation unit or the like for transporting the check target, or may be provided integrally with the absorption probe so as to apply the vibration at the time of the absorption. It is preferable that, if the vibration applier is provided integrally with the absorption probe, the vibration applier be positioned within an absorption aperture of the absorption probe such that the vibration-applying edge directly comes into contact with the check-target surface. Also, it is preferable that a slit for making it easier to absorb the air be provided on an aperture circumferential-wall of the absorption probe.

These embodiments permit a special drug adhering to the check-target surface to be liberated by the vibration, thereby making it possible to absorb the special drug into the mass spectrometer. This permits the sample pick-up to be easily performed, and simultaneously makes it possible to increase the sample-gas concentration. Incidentally, even if the liberated special drug is a powdery substance, the special drug need not be specially heated before being absorbed into the ion-source of the mass spectrometer. This is because the ion-source is usually heated at 100 to 300° C.

Also, as another method of liberating the special drug adhering to the surface of the check target, a method is applicable which injects the air onto the surface of or the proximity to the check target. Namely, injecting the air onto the surface of the check target liberates the special drug adhering to the surface. As a result, by absorbing the liberated sample, the sample can easily be guided into the mass spectrometer. For example, a small amount of explosive substance or drug, in many cases, adheres to the surface of clothes of a person who has recently treated the explosive substance or drug. Accordingly, by injecting the air onto the clothes so as to liberate the special drug adhering thereto, the special drug can be absorbed into the mass spectrometer.

This method of liberating by the air-injection and absorbing the special drug adhering to the surface of the check target can be embodied by providing a jet nozzle for jetting the air onto the surface of or the proximity to the check target, and the absorption nozzle for absorbing, as the sample gas, the air on the surface of or in the proximity to the check target. In this case, it is preferable that the absorption nozzle be provided in the surroundings of the jet nozzle. In particular, the following configuration is preferable: The inner pipe of a concentrically formed double-layered pipe is selected as the jet nozzle, and the outer pipe thereof is selected as the absorption nozzle. Moreover, the aperture end of the jet nozzle is located at a position of being a little retreated from the aperture end of the absorption nozzle. Also, a slit for making it easier to absorb the air is provided on an aperture circumferential-wall of the absorption nozzle.

Incidentally, the use of the vibration or the air-injection also liberates dusts in addition to the special drugs. Consequently, it is preferable that a step of removing the dusts from the absorbed surrounding-air by using a comparatively coarse-mesh filter or the like be provided before the ionization step.

Furthermore, as still another method of liberating the special drug adhering to the surface of the check target, a method is applicable which locally heats the surface of or the proximity to the check target. Namely, heating the surface of the check target by irradiating the surface with laser light or heat wave generates vapors of the check target, thereby making it possible to absorb the vapors into the mass spectrometer. This method can be embodied by providing a heating unit for locally heating the surface of or the proximity to the check target, and the absorption nozzle for absorbing, as the sample gas, the air on the surface of or in the proximity to the check target. Here, a unit for heating the surface of the check target by the heat wave is applicable as the heating unit. In particular, it is preferable that the heating unit by the heat wave be provided integrally with the absorption nozzle. Still in particular, it is preferable that a heating head be located in being positioned within an absorption aperture of the absorption nozzle, and that a slit for making it easier to absorb the air be provided on an aperture circumferential-wall of the absorption nozzle.

Also, the above-described air-jet nozzle, vibrator, or heating unit is provided integrally with the absorption nozzle. This makes it possible to configure the portable-type absorption probe. In this case, the absorption probe is configured to include a filter such as a piece of filter paper attached on the absorption-flow path in an attachment/detachment-fully-capable manner into/from the path. This configuration makes it possible to collect the sample of a powdery substance on the filter, or to pick up vapors of the sample in a state of being condensated on the filter. According to this characteristic, the filter on which the sample has been picked up is stored in a heater which is continuously-communicated to the ionization unit, thereby allowing the sample gas to be supplied to the mass spectrometer in a state of being enriched.

Other objects, features and advantages of the invention will become apparent from the following description of the embodiments of the invention taken in conjunction with the accompanying drawings.

BRIEF DESCRIPTION OF THE DRAWINGS

FIG. 6A is a cross-sectional view thereof, and FIG. 6B is a plane view thereof at the time of the operation;

FIG. 7 illustrates processing steps of an embodiment of a special drug detection method according to the present invention;

FIGS. 8A and 8B are diagrams for explaining effects by a spacing between the absorption heating plate and the opposed heating plate of the heater in FIG. 5;

DESCRIPTION OF THE INVENTION

Hereinafter, the explanation will be given below concerning embodiments of the present invention.

(First Embodiment)

Figure 1:
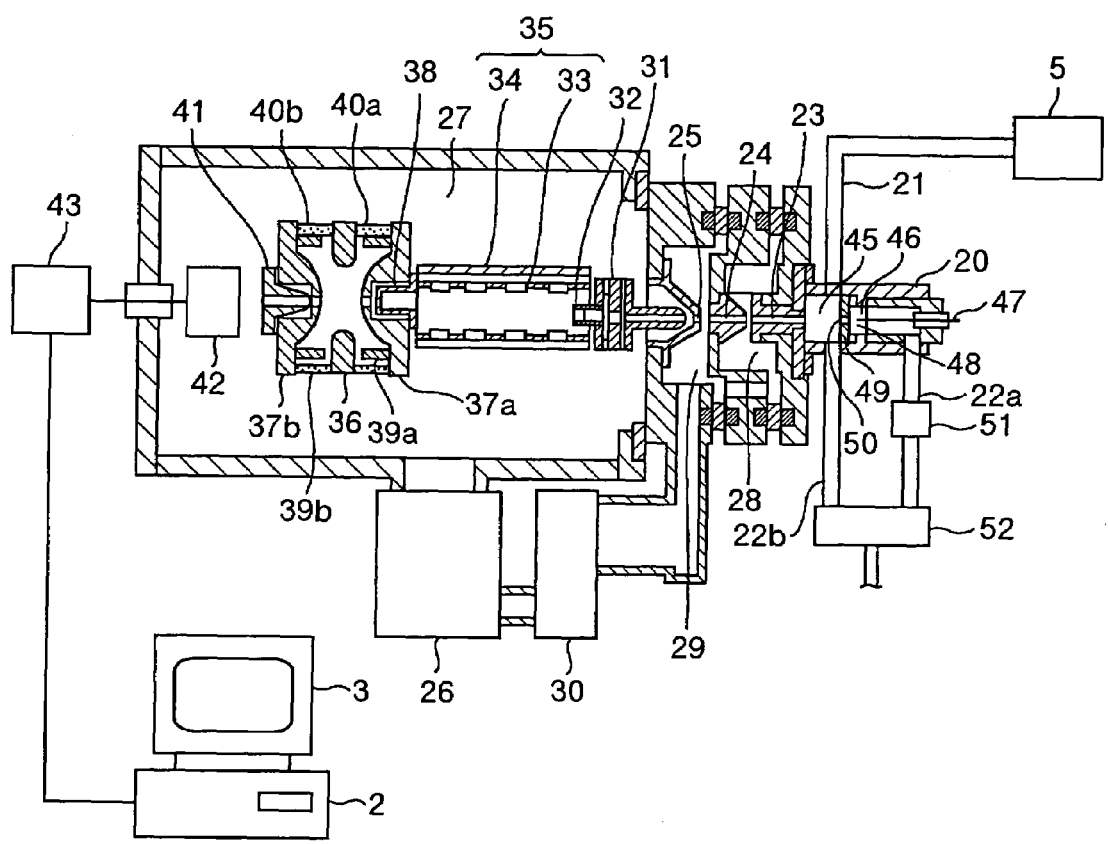
FIG. 1 is a configuration diagram for illustrating the main unit of a special drug detection device of an embodiment to which the present invention is applied.
Figure 2:
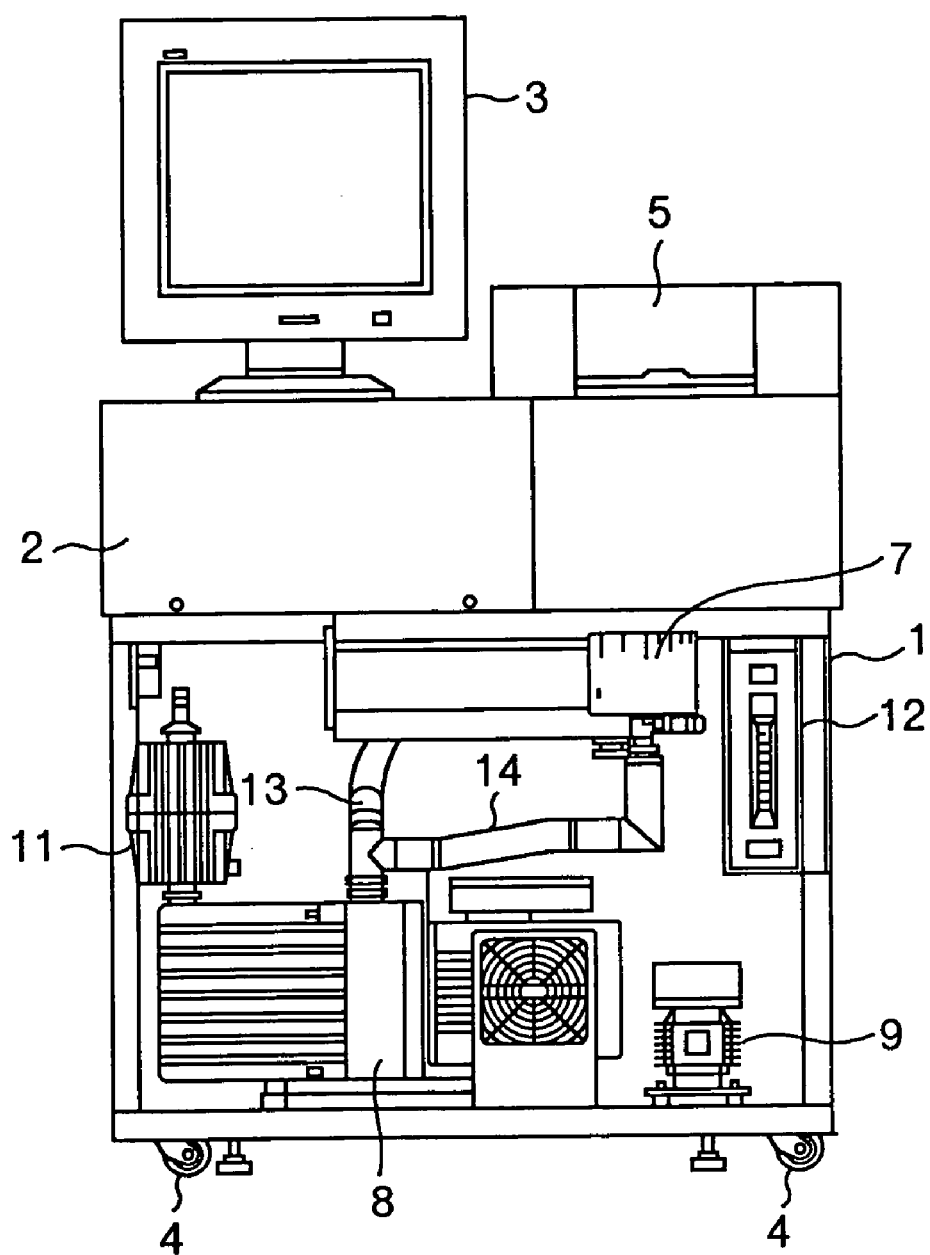
FIG. 2 illustrates an outside-appearance front view of the detection device of the embodiment in FIG. 1.
Figure 3:
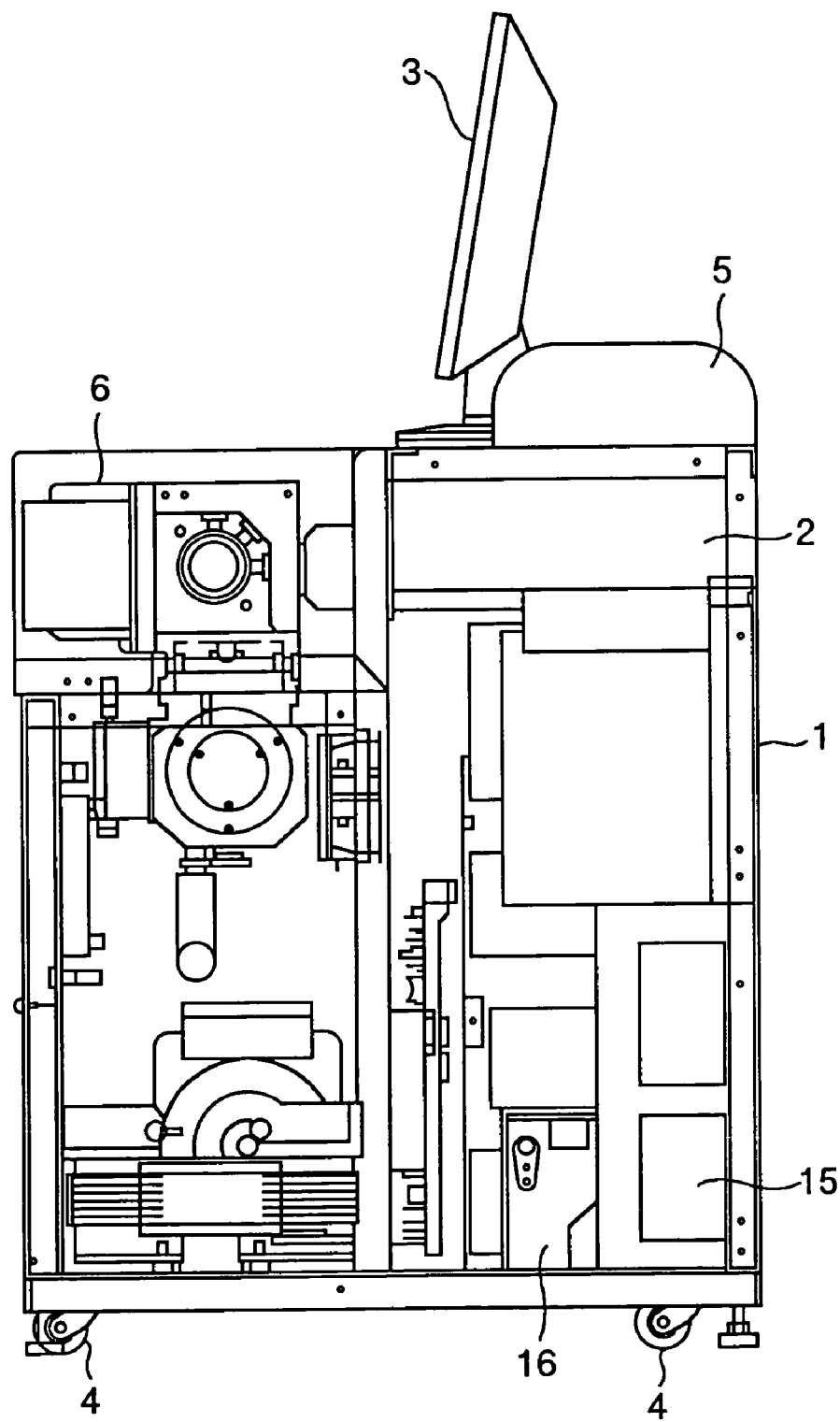
FIG. 3 illustrates a right side view of the detection device of the embodiment in FIG. 1.
Figure 4:
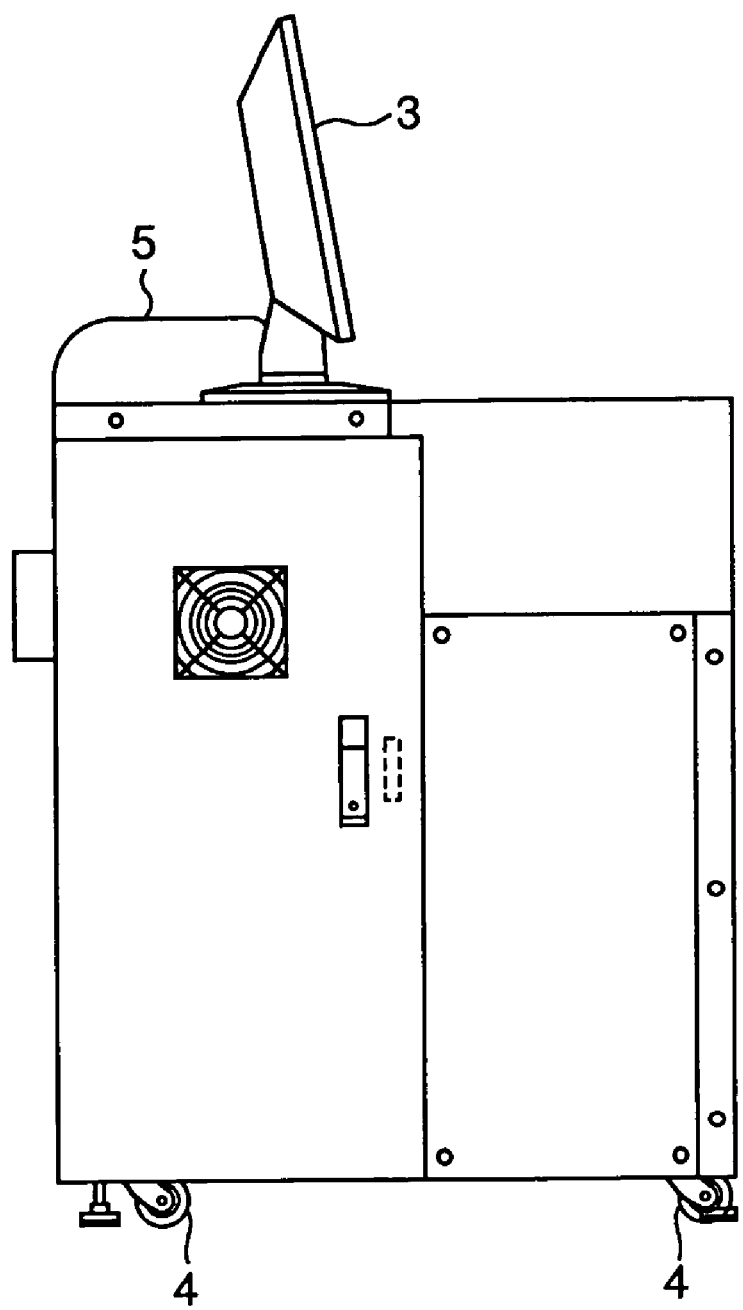
FIG. 4 illustrates a left side view of the detection device of the embodiment in FIG. 1.
Figure 5:
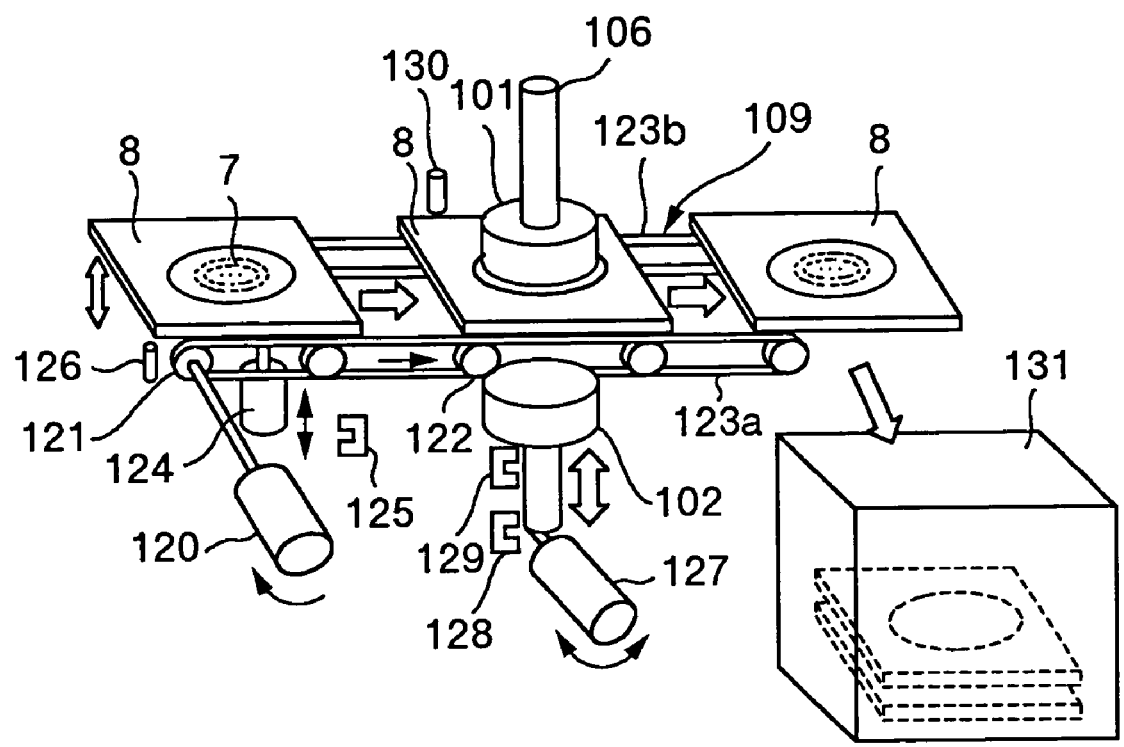
FIG. 5 is a perspective view for illustrating the entire configuration of a heater of the embodiment in FIG. 1.

FIG. 1 is a configuration diagram for illustrating the main unit of a special drug detection device of an embodiment to which the present invention is applied. FIG. 2, FIG. 3, and FIG. 4 illustrate an outside-appearance front view of the present embodiment, a right side view thereof, and a left side view thereof, respectively. FIG. 5 to FIG. 7 illustrate a check-chip heater associated with characteristics of the present invention.

As illustrated in FIG. 2, the detection device of the present embodiment includes a main body 1 that stores therein a mass spectrometer 6, a data processing device 2, a display device 3, and the like. Casters 4 are provided at the bottom of the main body, which makes the detection device transportable. A heater 5 is provided on the upper portion of a housing of the main body 1. Also, in the drawing, the reference numerals denote the following configuration components: 7 a vacuum pump (: 26 in FIG. 1), 8 a roughing pump (: 30 in FIG. 1), 9 an air pump, 10 a cooling fan, 11 an oil-mist collector, 12 a mass-flow meter, 13, 14 exhaust-flow paths, 15 a data control unit, and 16 a UPS. A rotary pump and a turbo molecular pump are provided in front of the main body 1. At the rear of the main body 1, the USP and a helium cylinder are stored in addition to the data processing device 2.

As illustrated in FIG. 1, a quadrupole ion-trap mass spectrometer (which, hereinafter, will be described as "ion-trap mass spectrometer") has been applied as the mass spectrometer 6 stored in the main body 1. A sample-gas introduction pipe 21 and exhaust pipes 22a and 22b are connected to an ion-source 20. The heater 5 is connected to one end of the sample-gas introduction pipe 21. Thus, a sample gas generated inside the heater 5 is introduced into the ion-source 20 by being absorbed using a not-illustrated pump connected to the exhaust pipes 22a and 22b. Part of the components contained in the sample gas introduced into the ion-source 20 is ionized. Namely, the sample gas introduced via the sample-gas introduction pipe 21 is introduced into an ion drift unit 45 at one time. This ion drift unit 45 lies in a substantially atmospheric-pressure state. Next, part of the sample gas introduced into the ion drift unit 45 is introduced into a corona discharge unit 46. The remaining sample gas is exhausted outside the ion-source via the exhaust pipe 22b. Moreover, the sample gas introduced into the corona discharge unit 46 is introduced into a corona discharge region 48, thereby being ionized. Here, the corona discharge region 48 is generated near the front end of a needle electrode 47 by applying a high voltage to the needle electrode 47. At this time, the sample gas is introduced into the corona discharge region 48 in a direction which is substantially opposed to the ion flow drifting from the needle electrode 47 toward an opposed electrode 49.

The ions generated in the corona discharge region 48 are introduced into the ion drift unit 45 by the electric field via an aperture portion 50 of the opposed electrode 49. At this time, a voltage is applied between the opposed electrode 49 and an electrode that forms therein the aperture of a first orifice 23. This allows the ions to be drifted, thereby making it possible to guide the ions into the first orifice 23 with a high efficiency. Next, the ions introduced from the first orifice 23 are introduced into a vacuum unit 27 via a second orifice 24 and a third orifice 25. Namely, the ions generated by the ion-source 20 and the part of the sample gas introduced into the ion-source are taken via the first orifice 23, the second orifice 24, and the third orifice 25 into the vacuum unit 27 exhausted by the vacuum pump 26. These orifices are about 0.3 mm in diameter, and the electrodes that form therein the apertures of these orifices are heated at about 100 to 300° C. by a not-illustrated heater. Meanwhile, the sample gas which has not been taken in from the first orifice 23 is exhausted outside the device via the pump from the exhaust pipes 22a and 22b. The spaces between the electrodes that form therein the apertures of the orifices 23, 24, and 25 have each become differential exhaust units 28 and 29, from which the exhaust is performed by the roughing pump 30 which is continuously-communicated to the differential exhaust unit 29. Although, as the roughing pump 30, a rotary pump, a scroll pump, or a mechanical booster pump is usually employed, the turbo molecular pump is also employable for exhausting this region. Also, a voltage is configured to be applied to the electrodes that form therein the apertures of the orifices 23, 24, and 25. This makes it possible to enhance the ion transmittance ratio, and simultaneously allows cluster ions, which are generated by the adiabatic expansion of the ions, to be opened/split by the collision with the molecules that turn out to remain.

In FIG. 1, a scroll pump whose exhaust rate is equal to 900 liters/minute has been employed as the roughing pump 30, and a turbo molecular pump whose exhaust rate is equal to 300 liters/minute has been employed as the vacuum pump 26 for exhausting the vacuum unit 27. The roughing pump 30 is in co-use as a pump as well for exhausting the back-pressure side of the turbo molecular pump. The pressure between the second orifice 24 and the third orifice 25 is equal to about 1 Torr. Also, by eliminating the electrode that forms therein the aperture of the second orifice 24, it is possible to configure the differential exhaust units using the two orifices, i.e., the first orifice 23 and the third orifice 25. In this case, the gas amount flown therein is increased in comparison with the case where there exists the electrode that forms therein the aperture of the second orifice 24. This necessitates the implementation of some device, e.g., increasing the exhaust rates of the pumps used, or setting the distance between the orifices apart. Also, in this case as well, it is important to apply a voltage between both of the orifices.

The ions generated by the ion-source 20, after having passed through the third orifice 25, are converged by a convergence lens 31. As this convergence lens 31, an Einzel lens which usually includes three sheets of electrodes or the like is employed. The ions are converged onto an aperture portion of a slit electrode 32 by the convergence lens 31, then passing through this aperture portion. Here, the structure is such that a neutral particle or the like which cannot be converged by the convergence lens 31 collides with the slit electrode 32 and finds it difficult to reach the mass-analysis-unit side. Next, the ions having passed through the slit electrode 32 in this way are deflected and converged by a double-layered-cylinder-type deflector 35 which includes an inner-cylinder electrode 33 equipped with a large number of aperture portions and an outer-cylinder electrode 34. In the double-layered-cylinder-type deflector 35, the deflection and convergence are performed using an electric-field by the outer-cylinder electrode which seeps through from the aperture portions of the inner-cylinder electrode, the details of which have been disclosed in JP-A-7-85834.

The ions having passed through the double-layer-cylinder-type deflector 35 are introduced into the ion-trap mass spectrometer which includes a ring electrode 36 and end-cap electrodes 37a and 37b. A gate electrode 38 is provided for controlling a timing of the ion incidence into the mass spectrometer. Brim electrodes 39a and 39b are provided for preventing the ions from reaching and charging quartz rings 40a and 40b for holding the ring electrode 36 and the end-cap electrodes 37a and 37b.

A not-illustrated helium-gas supply pipe supplies helium to the inside of the ion-trap mass spectrometer, thereby maintaining the inside pressure at about $10^{-3}$ Torr. Also, a not-illustrated mass-spectrometer control unit controls the ion-trap mass spectrometer. The ions introduced into the inside of the mass spectrometer collide with the helium gas to lose their energy, thus being captured by an alternating electric-field formed by a high-frequency voltage applied to the ring electrode 36 and the end-cap electrodes 37a and 37b. Next, by scanning the high-frequency voltage applied to the ring electrode 36 and the end-cap electrodes 37a and 37b, the captured ions are ejected from a orifice of the end-cap electrode 37b, depending on the m/z values of the ions. Moreover, the ejected ions reach a detector 42 via an ion extraction lens 41, then being detected. The detected signal, after being amplified by an amplifier 43, is inputted into the data processing device 2 so as to be processed.

The ion-trap mass spectrometer has a characteristic of capturing the ions within the space surrounded by the ring electrode 36 and the end-cap electrodes 37a and 37b. As a result, even if the concentration of the detection target substance is low and thus the ion amount generated is small, it becomes possible to detect the detection target substance by lengthening the introduction time of the ions. Consequently, even if the sample concentration is low, the high-magnification enrichment of the ions can be implemented at the stage of the ion-trap mass spectrometer. This makes it possible to exceedingly simplify sample's preprocessings (e.g., enrichment).

Here, the flow amount of the sample gas flown into the corona discharge unit 46 is important in order to detect a special drug with a high sensitivity and a high stability. On account of this, it is advisable that the exhaust pipe 22a be equipped with a flow-amount control unit 51. Also, it is advisable that, from the viewpoint of preventing the adsorption of the sample, the ion drift unit 45, the corona discharge unit 46, the sample-gas introduction pipe 21, and the like be heated beforehand by a heater (not illustrated) or the like. The gas flow-amount that passes through the sample-gas introduction pipe 21 or the exhaust pipe 22b can be determined by the capacity of an absorption pump 52 such as a diaphragm pump and the conductances of the above-described distribution pipes. It is advisable, however, that the sample-gas introduction pipe 21 and the exhaust pipe 22b be also equipped with a control device such as the flow-amount control unit 51. The absorption pump 52 is provided at a downstream position of the corona discharge unit 46 which, judging from the gas flow, is the ion generation unit. This reduces influences by a contamination (e.g., adsorption of the sample) of the inside of the absorption pump 52.

Figure 6A:
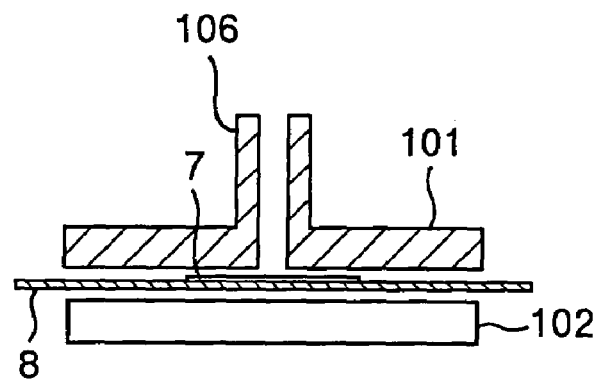
FIGS. 6A and 6B are detailed diagrams for illustrating an absorption heating plate and an opposed heating plate of the heater in FIG. 5.
Figure 6B:
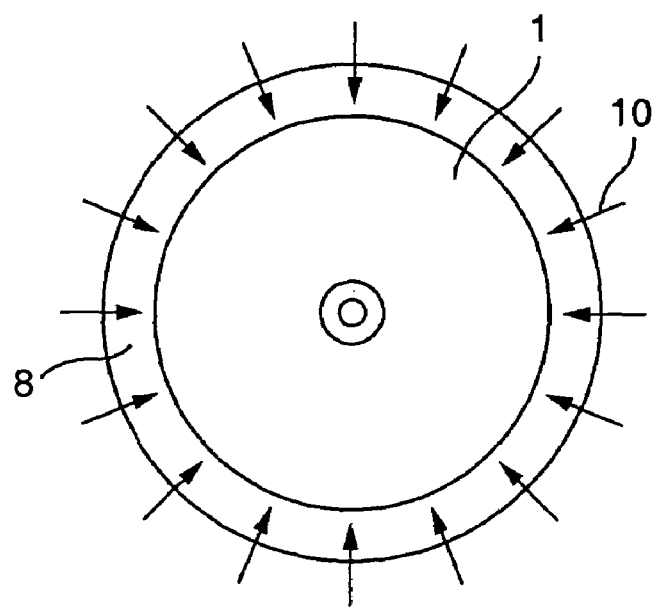

Here, referring to FIG. 5 to FIG. 7, the explanation will be given below concerning an embodiment of the heater 5 associated with the characteristics of the present invention. FIG. 5 illustrates the entire configuration of the heater 5 by a perspective view thereof. As illustrated in FIG. 5 and FIGS. 6A and 6B, the main-body unit of the heater 5 is formed by including a circular-plate-shaped absorption heating plate 101, and an opposed heating plate 102 which is held opposedly to this absorption heating plate 101 with a predetermined spacing apart. A penetration hole is provided in the central portion of the absorption heating plate 101, and a distribution pipe 106 is connected to this penetration hole. The other end of this distribution pipe 106 is connected to the sample-gas introduction pipe 21 in FIG. 1. Here, the opposed heating plate 102 is supported in a lift-up/lift-down-capable manner by a driving device 127. This allows the spacing with the absorption heating plate 101 to be adjustably formed. Also, the absorption heating plate 101 and the opposed heating plate 102 are heated and maintained at a predetermined high temperature by a heating unit and a temperature adjustment unit not illustrated. As illustrated in FIG. 6A, a check chip 8 on which a sample 7 has been picked up by wiping out the surface of a check target is inserted into a clearance between the absorption heating plate 101 and the opposed heating plate 102 configured as described above.

In the present embodiment, a transportation device 109 illustrated in FIG. 5 inserts the check chips 8 into the clearance between the absorption heating plate 101 and the opposed heating plate 102, thereby allowing the implementation of the continuous heating. Namely, the transportation device 109 includes the following configuration components: A pair of transportation driving pulleys 121 driven by a driving motor 120, plural dependent-movement pulleys 122, and two sheets of transportation belts 123a and 123b wound around the transportation driving pulleys 121 and the dependent-movement pulleys 122. The transportation belts 123a and 123b are rotated by the driving motor 120 in a direction of, e.g., an illustrated arrow 110. A lift-up/lift-down support device 124 for supplying the check chips 8 onto the transportation belts 123a and 123b is provided at the upstream end of the transportation belts 123a and 123b. When a check chip 8 is placed on board an on-board plane of the lift-up/lift-down support device 124, a detector 126 detects that the check chip 8 has been placed on board. At this time, if the check chip 8 has been in a state where the front-and-reverse, right-and-left, or back-and-forth relation is opposite and wrong, the on-board itself will not be detected.

The on-board plane of the lift-up/lift-down support device 124 is formed and set as follows: At the lifted-up position, the on-board plane is positioned above the upper-end planes of the transportation belts 123a and 123b. At the lifted-down position, the on-board plane is positioned below the upper-end planes of the transportation belts 123a and 123b. Moreover, lifting down the lift-up/lift-down support device 124 allows the check chip 8 to be placed on board the transportation belts 123a and 123b. If the check chip 8 has been lifted down, a lift-down detector 125 detects this. The width of the spacing between the transportation belts 123a and 123b is as follows: The width is a one that the check chip 8 can spread over, and the width is set to be a dimension larger than the outer diameter of the opposed heating plate 102. Also, the upper-end planes of the transportation belts 123a and 123b are set such that, at a position where the opposed heating plate 102 has been lifted down most by the driving device 127, the check chip 8 will be positioned away from the absorption heating plate 101 sufficiently. Incidentally, it is preferable that an O ring or a zone belt formed of a rubber-based material capable of acquiring an appropriate friction be used as the transportation belts 123a and 123b. Additionally, although a driving device such as a solenoid or an air cylinder is available in substitution for the driving motor 120 of the transportation device 109, an AC servo motor or a pulse motor is effective in the case of performing the precise positioning or controlling plural points.

The check chips 8 placed on board the transportation belts 123a and 123b are transported in the direction of the illustrated arrow 110, then being transported down to the position at which the absorption heating plate 101 and the opposed heating plate 102 are opposed to each other. Here, as will be described later, the check chips 8 are heated by the absorption heating plate 101 and the opposed heating plate 102. Also, a check-chip collection box 131 is set up under the downstream end of the transportation belts 123a and 123b.

Next, the explanation will be given below regarding the operation of the heater 5 in FIG. 5 configured in this way. At the time of the start, the lift-up/lift-down support device 124 is at the lifted-up position, and is on stand-by in a state of being capable of placing a check chip 8 on board the on-board plane of the device 124. Then, if the check chip 8 has been placed on board, the detector 126 is switched ON to lift down the lift-up/lift-down support device 124. This lift-down causes the check chip 8 to be placed on board the transportation belts 123a and 123b, thereby starting the transportation. When the check chip 8 has been transported, the detector 126 is switched OFF to stop the lift-down of the lift-up/lift-down support device 124. The termination of this lift-down is performed by the detector 125.

When the check chip 8 had been transported in the direction of the illustrated arrow 110, and has been transported down to the position at which the absorption heating plate 101 and the opposed heating plate 102 are opposed to each other, a detector 130 detects this, then halting the transportation belts 123a and 123b. In synchronization with this halt, the driving device 127 operates such that the opposed heating plate 102 will be lifted up to a position at which the spacing with the absorption heating plate 101 has become a predetermined spacing. If the opposed heating plate 102 has been lifted up to the predetermined position, a detector 129 detects this, then starting the measurement. Namely, the absorption heating plate 101 and the opposed heating plate 102 heat the check chip 8, thereby evaporating the sample 7 adhering to the check chip 8. Then, the evaporated sample gas is introduced into the ion-source 20 by a negative pressure via the distribution pipe 106 and the sample-gas introduction pipe 21. At this time, the surrounding air is absorbed as a carrier gas via the clearance between the absorption heating plate 101 and the opposed heating plate 102. In this way, the gas of the sample 7 adhering to the check chip 8 is eventually introduced into the mass spectrometer, where the mass analysis thereof is performed. Additionally, assuming the sample 7 which is of fast vaporization nature, the measurement may be started before the detector 129 detected the termination of the above-described lift-up, e.g., from the point-in-time when the opposed heating plate 102 had started to be lifted up.

After a predetermined analysis time has elapsed after the lapse of a predetermined heating (i.e., vaporizing) time, the driving device 127 is driven so as to lift down the opposed heating plate 102. This lift-down completion is confirmed by a detector 128. If the opposed heating plate 102 has been lifted down, the check chip 8 is placed on board the transportation belts 123a and 123b again so as to be transported. Then, if the check chip 8 has reached the downstream end of the transportation belts 123a and 123b, the check chip 8 drops down into the check-chip collection box 131 so as to be collected. This terminates the above-described series of sequences.

Here, as illustrated in FIG. 5, during the vaporization and measurement of a check chip 8b, the next check chip 8a can be set on stand-by in a state of being placed on board the lift-up/lift-down support device 124. Accordingly, at the step where the check chip 8b whose measurement had been terminated is ejected out into the check-chip collection box 131, the next check chip 8a can be transported down to the position of the heater's main body. This makes it possible to tremendously shorten the time-interval between the heating steps. Also, once a check chip 8 has been set on the lift-up/lift-down support device 124, the check chip 8 is automatically collected into the check-chip collection box 131 after the termination of the checking. Consequently, the check chips 8 can be collected in a batch manner without collecting the check chips 8 on each checking basis. As a result, the operator has only to perform the operation of setting the check chips 8, which allows an enhancement in the throughput. Furthermore, waiting for the collection to be terminated is unnecessary, which allows an enhancement in the operation efficiency.

Here, based on FIG. 7, the explanation will be given below concerning processing steps of an embodiment of a special drug (e.g., explosive substance) detection method using the special drug detection device which includes the heater 5 of the present embodiment. At first, the outer surface of a piece of hand baggage or the like is wiped out by using the check chip 8 such as a filter paper, thereby picking up substances adhering to the outer surface onto the check chip 8 such as the filter paper (S1). Here, the check chip 8 is not limited to the filter paper, but may also be a piece of cloth.

Next, the check chip 8 with which the outer surface of the hand baggage or the like has been wiped out is set on the lift-up/lift-down support device 124 of the heater 5. This allows the substances such as drugs, which have been picked up on the check chip 8, to be heated (e.g., at about 100 to 300° C.) and vaporized (i.e., evaporated) (S2). This, further, allows the small amount of sample 7, which has been picked up on the check chip 8, to be effectively introduced into the mass spectrometer. At this time, the surrounding air (i.e., carrier gas) absorbed from the heater 5 is suppressed down to a small amount so that the sample gas generated from the check chip 8 will not be diluted in concentration.

As illustrated in FIG. 7, the mass analysis of the sample gas including the drugs vaporized in this way is executed by the following steps: A first analysis step S3 of acquiring mass spectrums, a first judgment step S4 of judging whether or not ions having a first characteristic m/z value are present on the basis of the mass spectrums acquired at the first analysis step S3, a second analysis step S5 of performing a tandem mass spectroscopy in correspondence with a judgment result acquired at the first judgment step S4, a second judgment step S6 of judging whether or not ions having a second characteristic m/z value are present on the basis of mass spectrums acquired by the tandem mass spectroscopy, and a notification step S7 of outputting an alarm in correspondence with a judgment result acquired at the second judgment step S6. Here, the measurement operation including the step S3 and the step S4 is referred to as "screening mode", and the measurement operation including the step S5 and the step S6 is referred to as "detailed-checking mode".

When performing the detection, at first, at the step S3, the mass analysis of ions generated from the sample gas is performed, thereby measuring the mass spectrums. Moreover, at the step S4, it is judged whether or not the ions having the first characteristic m/z value corresponding to ions which result from a special drug, i.e., the detection target, have been detected. For example, if molecules of amphetamine, i.e., a kind of stimulant, are ionized in a positive atmospheric-pressure chemical ionization mode, pseudo molecule ions $(M+H)^+$ (M: the sample molecule, H: proton) where the proton is added to the amphetamine molecule are produced. Since the m/z value of this pseudo molecule ion is equal to 136, it is judged at the step S4 whether or not ions whose m/z value is equal to 136 have been detected. Here, it is needless to say that the m/z value judged at the step S4 differs depending on the type of the special drug. Also, it is advisable that the presence or absence of plural different m/z values be judged in correspondence with various types of drugs, stimulants, and the like.

It is also advisable that, when the analysis time at the first analysis step S3 is assumed to be 0.1 second, the measurement at the step S3 be repeated and the judgment at the step S4 be made on a result acquired by making an integrated calculation of those measurement results. Making the integrated calculation averages random noises. This makes it possible to reduce a possibility of making an erroneous judgment at the step S4.

If, at the step S4, the ions having the first characteristic m/z value set up in advance have been judged to be present, the tandem mass spectrometry (which, hereinafter, will be described as "MS-MS") is executed at the second analysis step S5. The analysis step S5 includes the selection of precursor ions, the dissociation of the precursor ions, and the mass analysis of fragment ions. Also, it is advisable that, in order to enhance the analysis accuracy, a longer time be spent in the step S5 as compared with the step S3.

The MS-MS measurement at the step S5 allows the acquisition of the mass spectrums which include ample information about the molecular structures. The judgment step S6 judges these mass spectrums. This second judgment step judges whether or not the ions having the second m/z value characteristic of the detection target are present. If the ions are present, the alarm is outputted at the step S7 so as to notify the ions' presence. Incidentally, when making the judgment at the step S6, the mass spectrums of the detection target acquired by the tandem mass spectroscopy at the step S5 are utilized as a database. Making reference to this database allows the accomplishment of a higher-accuracy judgment.

In the case of the hand-baggage checking, it takes a certain extent of time to terminate the wiping-out operation using the check chip 8 such as a filter paper, and the setting operation of the check chip 8 onto the heater 5. An assumption, however, can be made that no special drug is contained in almost all the pieces of hand baggage. This, after the setting operation of the check chip 8 onto the heater 5, permits the detection to be terminated in about 1 second with the employment of the screening mode. Accordingly, the employment of the processing steps illustrated in FIG. 7 permits an average time needed for the detection to be suppressed down to about 1 to 2 seconds on each hand-baggage basis, although, on a rare occasion, it takes a little longer time to execute the processing steps up to the detailed-checking mode. Consequently, it becomes possible to check the pieces of hand baggage at a security gate without considerably hindering the flow of the pieces of hand baggage. Also, ultimately, the judgment based on the tandem mass spectroscopy is made by employing the detailed-checking mode. This allows the implementation of a high selectivity and a reduction in the number of false reports. By the way, since the detailed-checking mode necessitates the little longer time, the following measure is preferable: Namely, a signal which is easy for the operator to recognize, such as lighting up a warning lump, is outputted at the stage of having transitioned from the screening mode to the detailed-checking mode.

So far, the explanation has been given above concerning the first embodiment of the sample pick-up method including the heating method which is the characteristic of the present invention. Hereinafter, referring to FIG. 8A to FIG. 21D, the explanation will be given below regarding the other embodiments of the present invention.

(Second Embodiment)

The embodiment illustrated in FIG. 5 is as follows: The opposed heating plate 102 is configured to be in the lift-up/lift-down-capable manner. Next, the spacing between the opposed heating plate 102 and the absorption heating plate 101 is enlarged, then inserting the check chip 8 into the spacing therebetween. After that, the spacing is narrowed down to a predetermined spacing, then performing the measurement and the heating. In substitution for this, the following embodiment is preferable: The spacing between the opposed heating plate 102 and the absorption heating plate 101 is fixed beforehand, then inserting the check chip 8 into the clearance therebetween.

Figure 9A:
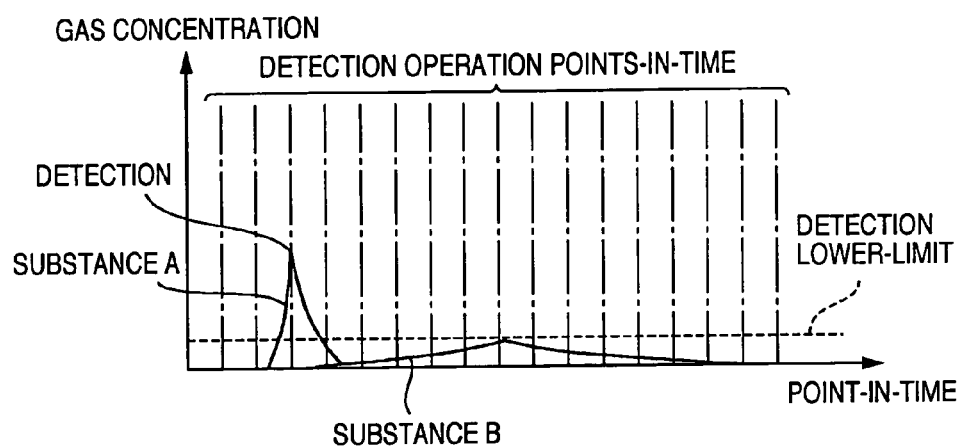
FIGS. 9A and 9B are line diagrams for explaining a time change in the concentration of a sample gas which changes by the spacing between the absorption heating plate and the opposed heating plate in FIG. 8.

Here, referring to FIGS. 8A and 8B, the explanation will be given below regarding influences exerted on the measurement by the spacing between the opposed heating plate 102 and the absorption heating plate 101. At first, for the explanation, the following assumption is made: Two types of substances A and B whose vapor pressures at one and the same temperature differ from each other are contained in the sample 7 in predetermined amounts respectively, and also the vapor pressure of the substance A is relatively higher as compared with that of the substance B. At first, the explanation will be given below regarding a case where, as illustrated in FIG. 8A, the spacing between the opposed heating plate 102 and the absorption heating plate 101 is fixed to be d1, and then the check chip 8 is inserted therein. In this case, FIG. 9A illustrates a time change in the concentration of the sample gas to be introduced into the ion-source 20 of the mass spectrometer from the heater 5. In FIG. 9A, a point-in-time when the check chip 8 had been inserted between the absorption heating plate 101 and the opposed heating plate 102 is defined and represented as 0. Also, the gas concentration is illustrated by being normalized using a detection lower-limit value which differs depending on the substances. The detection lower-limit value, which becomes a constant value by this normalization, is indicated by the dotted line. Also, in the mass spectrometer, the mass-analysis operation is usually performed by executing a sampling intermittently. Accordingly, points-in-time of the sampling period are indicated by the one-point chain lines.

Generally speaking, if the gas concentration of a substance to be introduced into the mass spectrometer has continuously exceeded a lower-limit value during a time-interval longer than a sampling period, the substance can be detected in any one of the samplings. On the other hand, if the gas concentration of the substance has not exceeded the lower-limit value in any one of the samplings after the introduction of the sample, the substance cannot be detected. In FIG. 9A, the substance A corresponds to the former case, and the substance B corresponds to the latter case. In this way, depending on differences in the vapor pressures of substances, the waveforms of time passages in the gas concentrations differ from each other. The reason for this phenomenon is as follows: Namely, a substance having a higher vapor pressure exhibits a higher vaporization rate in the heater 5, thereby generating a high-concentration gas in a short time. On the other hand, a substance having a lower vapor pressure exhibits a lower vaporization rate in the heater 5, thereby continuing to generate a low-concentration gas for a long time.

Figure 9B:
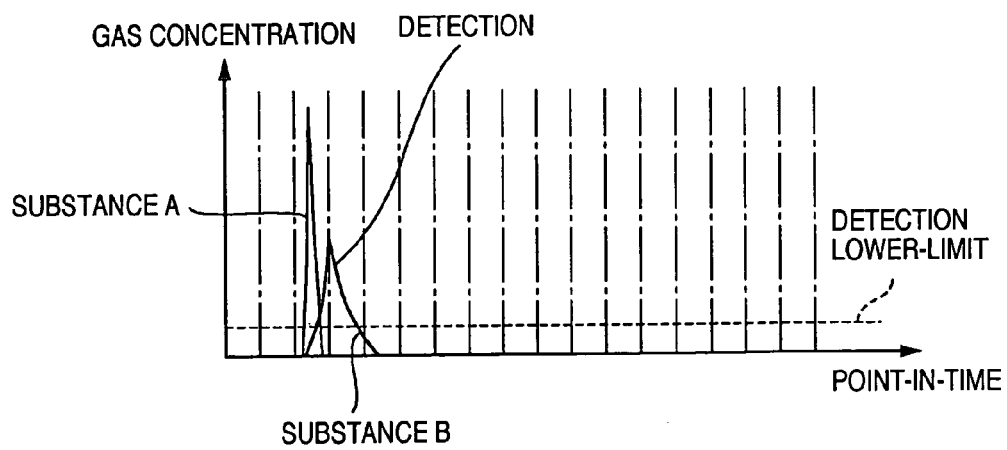

Next, the explanation will be given below regarding a case where, by lifting up the opposed heating plate 102, the spacing with the absorption heating plate 101 is narrowed down to d2 as is illustrated in FIG. 8B, and then the check chip 8 is inserted therein. FIG. 9B illustrates a time change in this case in the concentration of the sample gas to be introduced into the ion-source 20 of the mass spectrometer from the heater 5. As compared with the spacing between the absorption heating plate 101 and the opposed heating plate 102 in the case of FIG. 9A, the spacing has become narrower. This causes a speeding-up in the heating speed for the sample, thus resulting in a situation that, as for both of the substances A and B, the maximum values of the gas concentrations have been increased whereas the generation times have been shortened. In FIG. 9B, however, the substance B can be detected. As for the substance A, nevertheless, the vaporization thereof has been terminated in a time-interval shorter than the sampling period. Accordingly, the substance A may step aside from the sampling timing, and thus cannot be detected in some cases. Also, the opposed heating plate 102 is in contact with a surface of the check chip 8 to which the sample 7 does not adhere. It is needless to say that this condition speeds up the heating speed most.

Consequently, in the embodiment illustrated in FIG. 5, the opposed heating plate 102 is lifted up/lifted down by the driving device 127 so as to adjust the spacing with the absorption heating plate 101. This makes it possible to change the heating speed for the sample in the heater 5. This, further, allows a heating speed preferable for the detection to be easily implemented in accordance with the vapor pressure of a substance of the detection target.

Figure 10A:
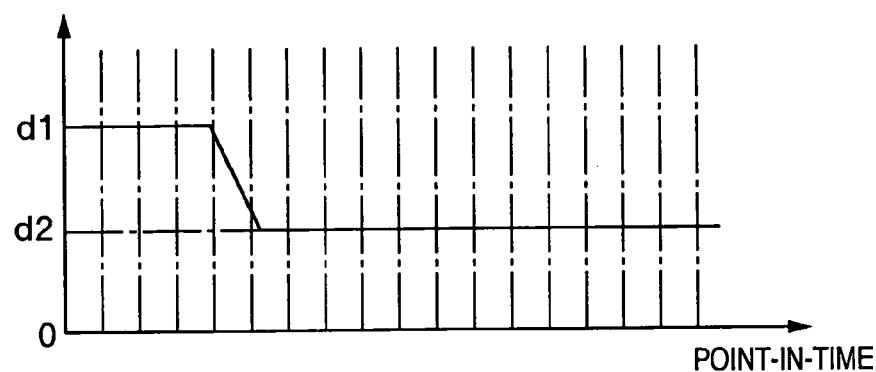
FIGS. 10A and 10B are line diagrams for explaining a time change in the concentration of the sample gas at the time when the spacing between the absorption heating plate and the opposed heating plate in FIG. 8 is changed.
Figure 10B:
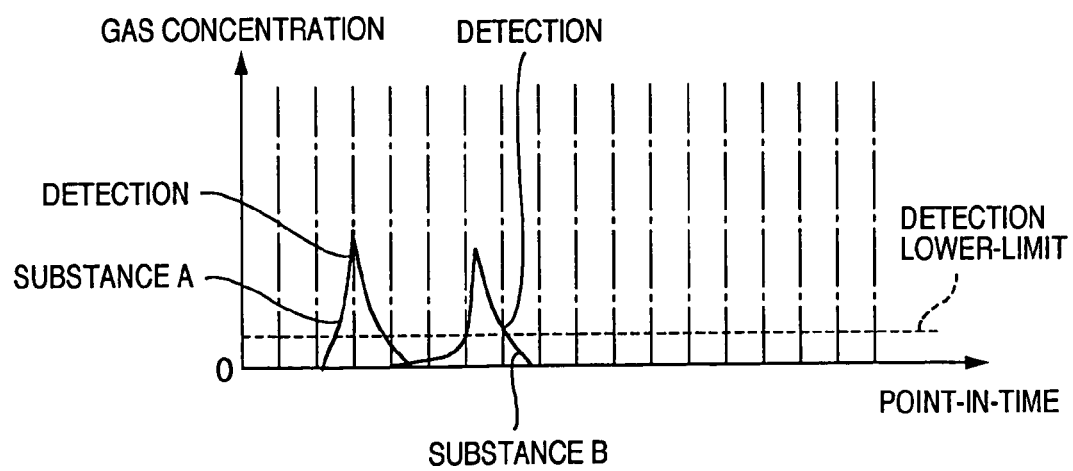

Next, in the embodiment illustrated in FIG. 5, the explanation will be given below regarding the following case: At a point-in-time when the check chip 8 was inserted into the spacing, the spacing had been in the state illustrated in FIG. 8A. After that, by lifting up the opposed heating plate 102 by the driving device 127, the spacing has fallen into the state illustrated in FIG. 8B. At first, FIG. 10A illustrates the change in the spacing between the absorption heating plate 101 and the opposed heating plate 102, and FIG. 10B illustrates a change in the gas concentration to be introduced into the mass spectrometer. As is shown from FIGS. 10A and 10B, at a point-in-time when the spacing was equal to d1, the substance A had been detected. After that, by lifting up the opposed heating plate 102 so as to narrow the spacing down to d2, the substance B having a lower vapor pressure has been detected. In this way, after the introduction of the sample, the opposed heating plate 102 is lifted up so as to narrow the spacing, thereby speeding up the heating speed. Accordingly, even if various types of substances having different vapor pressures are contained in one and the same sample, executing this speeding-up operation makes it possible to detect these substances easily.

(Third Embodiment)

Figure 11:
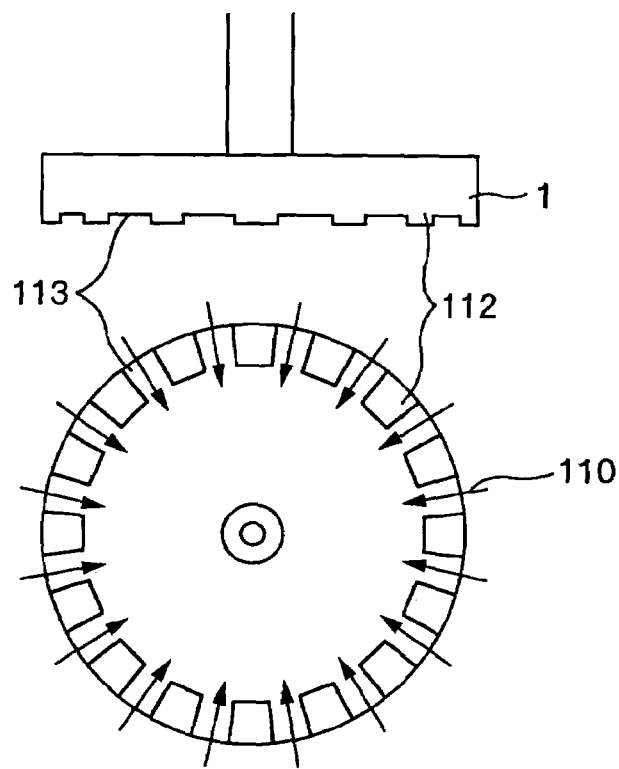
FIG. 11 is a detailed diagram for illustrating another embodiment of the absorption heating plate of the heater in FIG. 5, and there are illustrated a side view thereof and a rear view thereof.

FIG. 11 illustrates another embodiment of the main-body unit of the heater 5 including the absorption heating plate 101 and the opposed heating plate 102 according to the embodiment in FIG. 5. The present embodiment is as follows: The check chip 8 is fixed by being sandwiched between the absorption heating plate 101 and the opposed heating plate 102 through the contacts therewith, then vaporizing the sample 7. Namely, as illustrated in FIG. 11, protrusions 112 in a constant height are provided along the circumferential portion of the heating surface of the absorption heating plate 101 according to the present embodiment in a direction heading from the center to the circumferential direction. Between the respective protrusions 112, a groove-shaped absorption opening 113 is formed which is capable of absorbing the surrounding atmosphere-gas. The configuration of each absorption opening 113 is no specific problem, as long as each opening 113 is routed to the inside of the heating surface of the absorption heating plate 101 so that the sample gas can be absorbed in a necessary flow-amount. When the check chip 8 has been inserted into the lower-surface position of the absorption heating plate 101, the opposed heating plate 102 is lifted up, thereby bringing the check chip 8 into contact with the absorption heating plate 101 so as to be fixed thereon.

The present embodiment is effective in a case where the check chip 8 is formed of a soft material and thus the holding is unstable. Namely, the fixing of proximity to the measurement surface of the check chip 8 allows the sample 7 to be held in a flat and stable state. This makes it possible to stabilize the vaporization and to execute the mass analysis without measurement variations. Also, the heating surface of the opposed heating plate 102 is formed into a concave configuration, then adjusting the spacing with the absorption heating plate 101. This makes it possible to adjust the heating speed into a slowed-down value.

(Fourth Embodiment)

Figure 12:
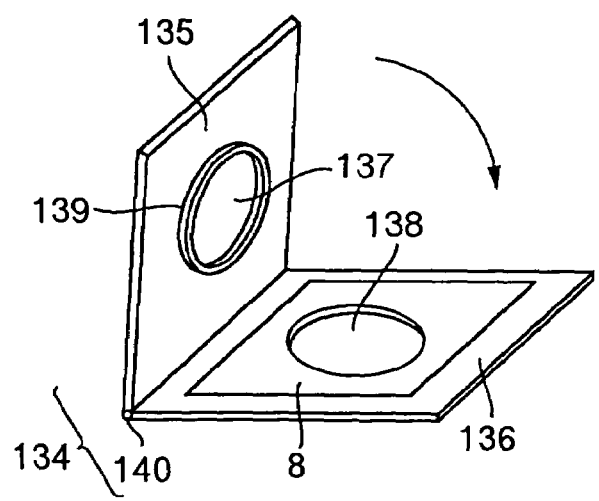
FIG. 12 is a perspective view for illustrating an embodiment of a holding equipment of a check chip.
Figure 13:
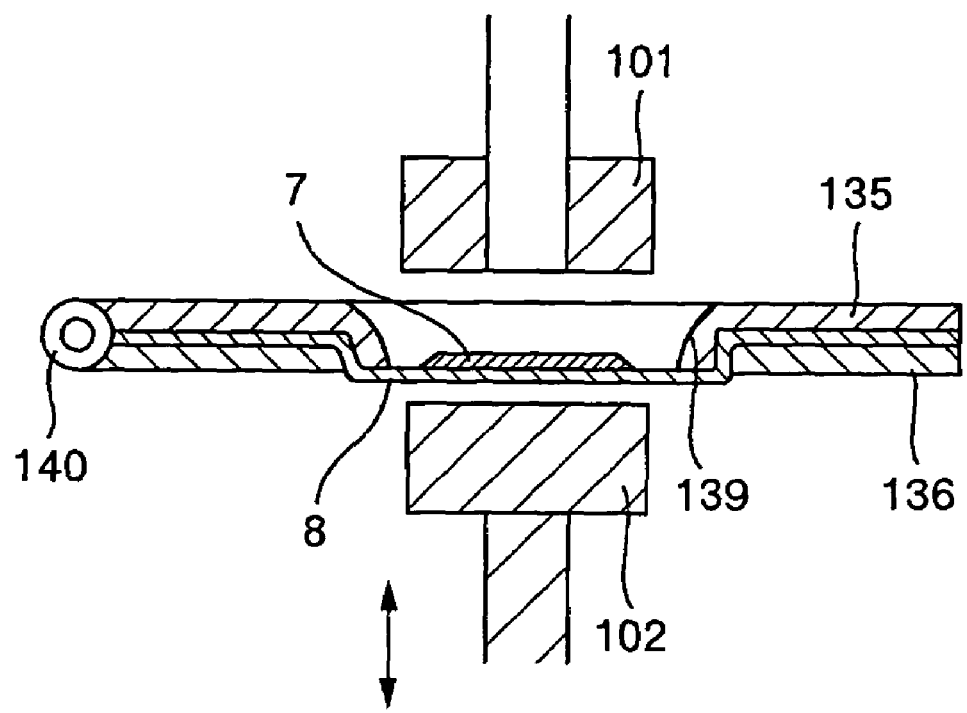
FIG. 13 is a side cross-sectional view for illustrating the check-chip holding equipment in FIG. 12.

FIG. 12 and FIG. 13 illustrate an embodiment of a holding equipment of the check chip 8. The present embodiment is a check-chip holding equipment which is preferable for the case where the check chip 8 formed of a soft material is heated by the heater 5 of the embodiment in FIG. 5. The check-chip holding equipment 134 is configured by connecting an upper holding equipment 135 and a lower holding equipment 136 by using a hinge 140. Circle-shaped apertures 137 and 138 whose diameters are larger than those of the absorption heating plate 101 and the opposed heating plate 102 are formed in the central portions of the upper holding equipment 135 and the lower holding equipment 136. A ring protrusion 139 is formed along the circumferential edge portion of this aperture 137 such that, when the upper holding equipment 135 and the lower holding equipment 136 are folded using the hinge 140, the outer circumference of the ring protrusion 139 will be inserted into the inside of the aperture 138 of the lower holding equipment 136 with a constant clearance left. The check-chip holding equipment 134 is formed of a material which is repeatedly usable, heat-resistant, and exerts an appropriate friction onto the transportation belts 123a and 123b in FIG. 5. The diameters of the apertures 137 and 138 are designed to an extent which prevents the upper holding equipment 135 and the lower holding equipment 136 from being heated too much by the absorption heating plate 101 and the opposed heating plate 102. Incidentally, the configurations of the apertures 137 and 138 may be either the circular shape or square shape, depending on those of the absorption heating plate 101 and the opposed heating plate 102.

The check-chip holding equipment 134 of the present embodiment has been configured in this way. Here, assume that the check chip 8 of a soft material is placed on board the lower holding equipment 136 with the surface to which the sample 7 adheres directed upwards, and that the upper holding equipment 135 is folded. As a result of this, on account of the above-described configuration, the check chip 8 is sandwiched by the ring protrusion 139 and the aperture 138 of the lower holding equipment 136. This smoothes out wrinkles of the check chip 8 formed at the time of the sample wiping-out or the like. As a consequence, it becomes possible to control the clearance between the absorption heating plate 101 and the opposed heating plate 102 and the spacing with the check chip 8, thereby allowing the execution of a stable and high-accuracy measurement. Also, it becomes possible to prevent an increase in contaminants caused by rubbing the periphery. Additionally, although the case has been given where the ring protrusion 139 is formed along the entire circumference of the aperture 137, it is also advisable that protrusions be provided along the circumferential edge portions of the aperture 137 and the aperture 138 in substitution for the ring protrusion 139. Also, it is advisable that the check chip 8 be smoothed out by providing protrusions on the opposed-side surfaces of the upper holding equipment 135 and the lower holding equipment 136.

(Fifth Embodiment)

Figure 14:
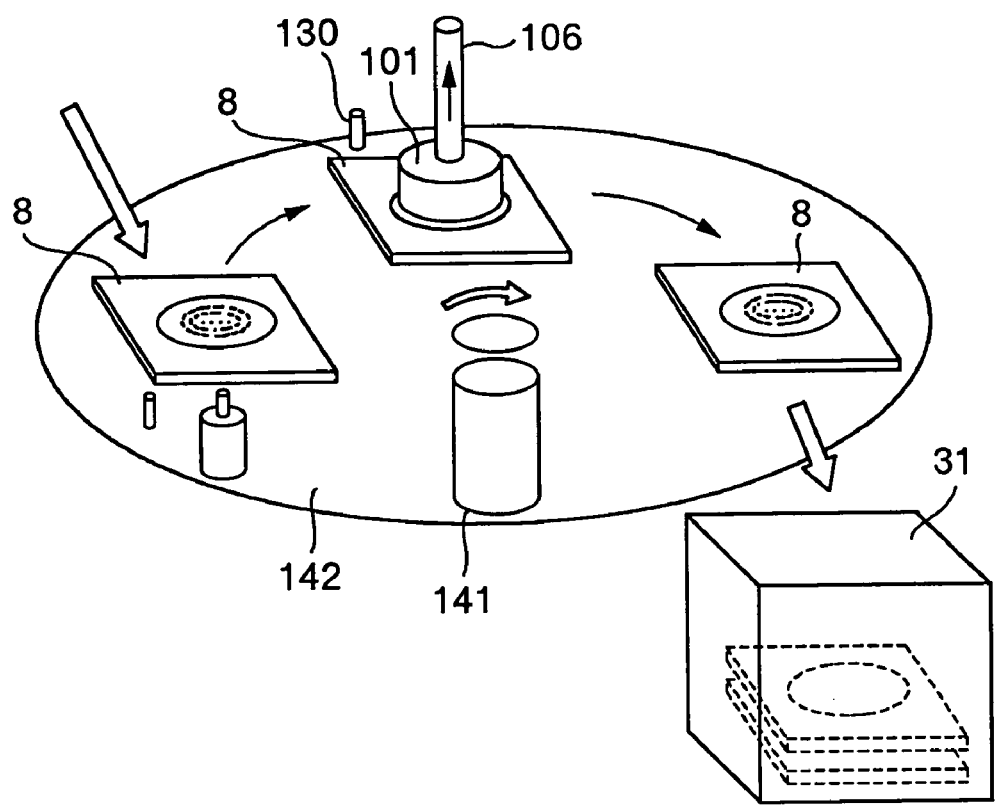
FIG. 14 is a perspective view for illustrating the entire configuration of another embodiment of the heater according to the present invention.

FIG. 14 illustrates, by a perspective view, the entire configuration of another embodiment of the heater 5 according to the present invention. The present embodiment is a one implemented by changing, to a rotation system, the transportation device 109 of the check chip 8 in the heater 5 illustrated in FIG. 5. Namely, a rotation plate 142 is selected as the transportation medium in substitution for the transportation belts 123a and 123b. The rotation plate 142 is rotation-driven by a motor 141. The driving control over the motor 141 allows the check chip 8 to be transported from the set position to the position of the check-chip collection box 131 via the clearance between the absorption heating plate 101 and the opposed heating plate 102. If this transportation operation is performed intermittently to make the transportation pitch constant in advance, similarly with the operation described earlier, setting the check chips 8 one after another makes it possible to perform the measurement continuously, and to eject the check chips 8 whose measurements have been terminated into the check-chip collection box 131. Incidentally, although not illustrated in the same drawing, an aperture whose diameter is larger than the outer diameters of the absorption heating plate 101 and the opposed heating plate 102 is provided in a location on the rotation plate 142 on which the check chip 8 is placed on board. The opposed heating plate 102 is lifted up/lifted down, thereby making adjustable the spacing with the absorption heating plate 101.

According to the first to fifth embodiments of the heater 5 explained so far, the absorption heating plate 101 and the opposed heating plate 102 are opposed to each other with a clearance formed therebetween. Then, the check chip 8, i.e., a target to be heated, is inserted therebetween so as to heat and vaporize the sample 7. Accordingly, the heater 5 is applicable to a check chip 8 which has no ventilation property. Also, the sample gas is absorbed therein in such a manner that the air introduced by a negative pressure of the ion-source 20 via the clearance between the absorption heating plate 101 and the opposed heating plate 102 is used as the carrier gas. Consequently, the gas flow of the sample gas is stabilized immediately after the check chip 8 has been inserted into the clearance between the absorption heating plate 101 and the opposed heating plate 102. This makes it possible to enhance the reliability of the detection. Also, even if plural substances having different vapor pressures are contained in the sample 7, it is possible to detect these substances easily. Furthermore, the check chips 8 are automatically transported into the clearance between the absorption heating plate 101 and the opposed heating plate 102, which allows an enhancement in the throughput. Simultaneously, waiting for the collection of the terminated check chips 8 is unnecessary, which allows an enhancement in the operation efficiency.

Incidentally, in the first to fifth embodiments, the explanation has been given concerning the case where the sample gas vaporized by heating the check chip 8 onto which the sample 7 has been wiped out is inserted into the ion-source 20 of the mass spectrometer. However, the sample pick-up method of the present invention is not limited thereto, but can employ the following embodiments described below:

(Sixth Embodiment)

Figure 15:
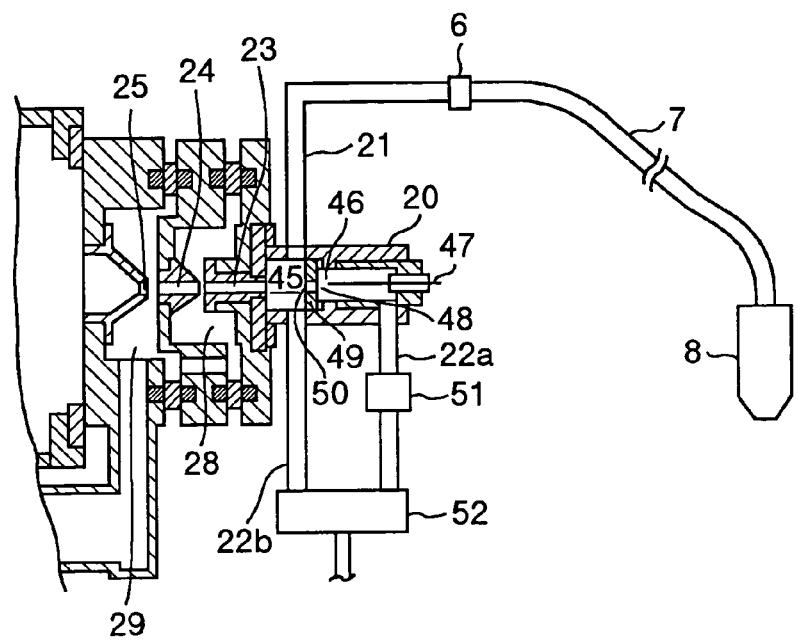
FIG. 15 is a diagram for illustrating another embodiment of the special drug sample detection method according to the present invention.

FIG. 15 illustrates another embodiment of the sample pick-up method of the present invention. The present embodiment differs from the previously-described pick-up method in a point that, in substitution for the heater 5 of the embodiment in FIG. 1, a hose connector 6 is mounted on the sample-gas introduction pipe 21, and an absorption hose 7 is connected to this hose connector 6, and an absorption probe 8 for picking up the sample gas is mounted on this absorption hose 7. Namely, the present embodiment is a one where, in substitution for the system of picking up the sample by wiping out the outer surface or the like of a check target with the check chip 8 such as a filter paper, the sample is directly absorbed from the outer surface or the like of the check target so as to be supplied into the mass spectrometer.

Figures 16A, 16B:
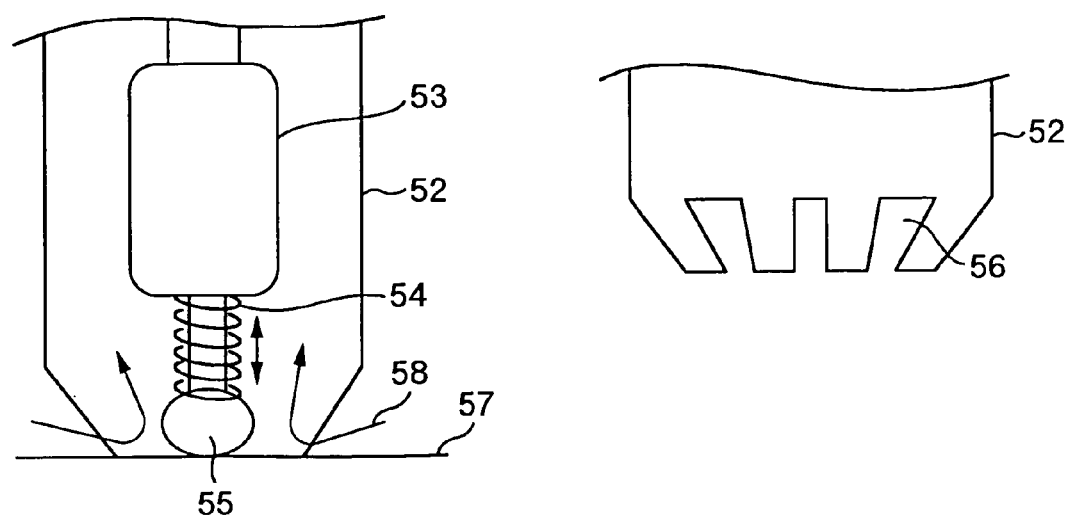
FIGS. 16A and 16B are diagrams for illustrating an embodiment of a vibrator-type absorption probe according to the present invention.

As concrete examples of the absorption probe 8, examples illustrated in FIGS. 16A and 16B, FIG. 17, and FIG. 18 can be employed. The absorption probe 8 illustrated in FIG. 16A is a vibrator-type absorption probe, which is configured as follows: A vibration generator 53 is provided inside a housing 52 whose front-end portion is tapered down. Moreover, a contact vibrator 55 is mounted on the vibration generator 53 via an elastic member 54 such as a spring in a step-back/step-forth-fully-capable manner in the direction of the housing 52. Also, as illustrated in FIG. 16B, slits 56 capable of absorbing the air are formed around the circumferential surface of the tapered-down portion at the front end of the housing 52.

On account of this configuration, if the vibration generator 53 is driven to bring the contact vibrator 55 directly into contact with the outer surface of the check target 57, substances adhering to the outer surface of the check target 57 are liberated by the vibration, then being absorbed into the absorption probe 8 by accompanying an absorption gas flow 58. The sample gas absorbed into the absorption probe 8 is introduced into the mass spectrometer via the absorption hose 7 and the sample-gas introduction pipe 21. Additionally, apertures of the slits 56 are determined so that the absorption air flow will occur which is of an extent allowing the liberated substances to be accompanied by the absorption air.

Figure 17:
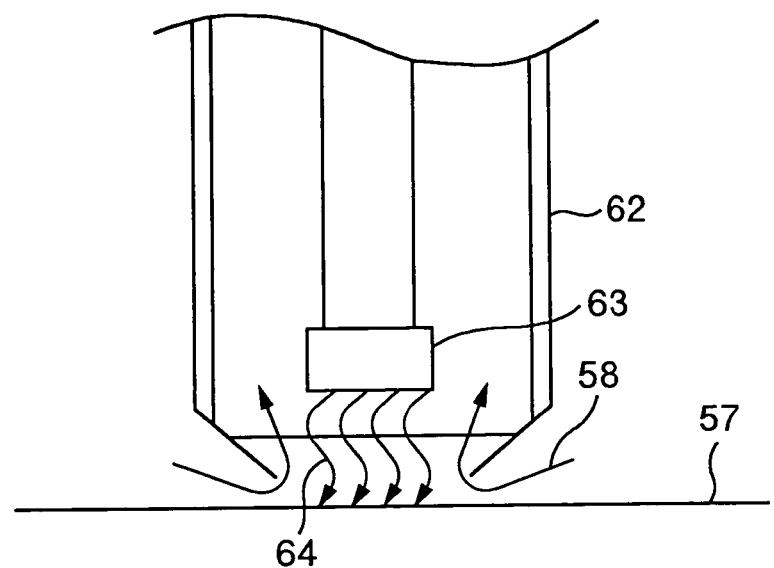
FIG. 17 is a diagram for illustrating an embodiment of a heating-type absorption probe according to the present invention.

Meanwhile, the absorption probe 8 illustrated in FIG. 17 is a heating-type absorption probe where, in substitution for the vibration generator 53 and the contact vibrator 55 in FIG. 16A, a heater 63 is provided at the front-end portion of the inside of a housing 62. This absorption probe is configured such that heat wave 64 from the heater 63 makes it possible to heat the surface of the check target 57. Also, an electric thermal wire for heating the inner surface is wound around the housing 62. On account of this configuration, according to the absorption probe 8 in FIG. 17, the substances adhering to the surface of the check target 57 are evaporated by the heat (e.g., about 80 to 100° C.) so as to be absorbed into the absorption probe 8, then being introduced into the mass spectrometer.

Figure 18:
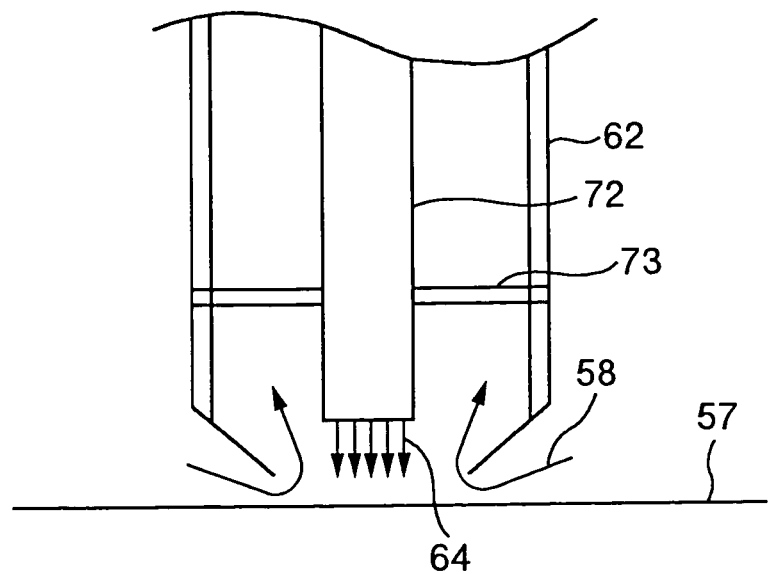
FIG. 18 is a diagram for illustrating an embodiment of a light-heating-type absorption probe according to the present invention.

Also, the absorption probe 8 illustrated in FIG. 18 is a light-heating-type absorption probe where, in substitution for the heater 63 in FIG. 17, the surface of the check target 57 is heated by irradiating the surface with light 64, such as laser light, with the use of an optical fiber 72. In the drawing, a reference numeral 73 denotes a support member for supporting the optical fiber 72, and configuration components to which the same reference numerals as the ones in FIG. 17 are attached have the same function configurations. On account of this configuration, according to the absorption probe 8 in FIG. 18, similarly with the case in FIG. 17, the substances adhering to the surface of the check target 57 are evaporated by the heat, and the vapors are introduced into the mass spectrometer.

Figure 19:
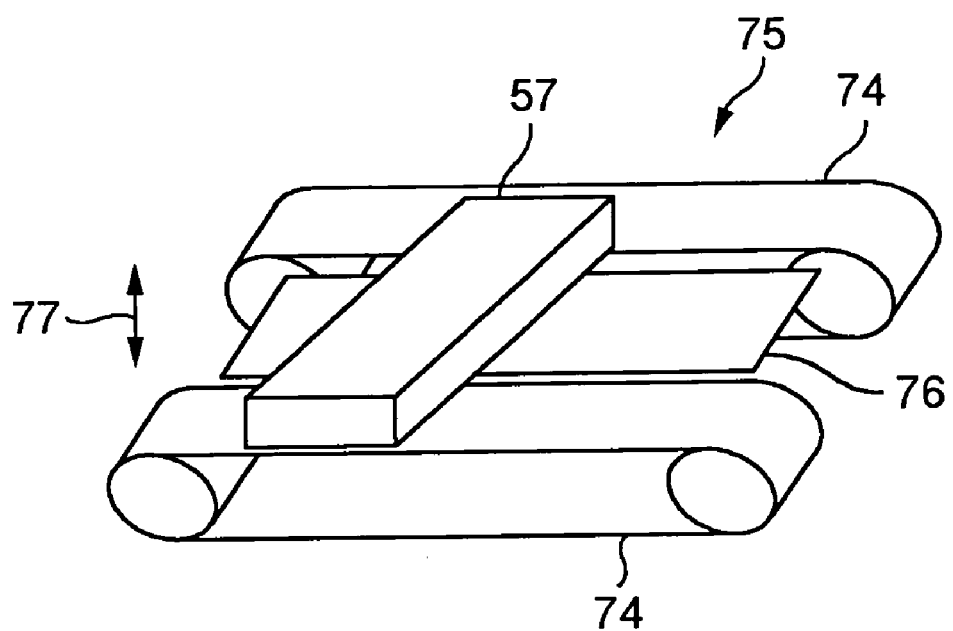
FIG. 19 is a diagram for illustrating an embodiment of a vibration-type transportation device according to the present invention.

FIG. 19 illustrates a modified embodiment of the pick-up method in FIG. 16A where the adhering substances to the check-target surface are picked up by utilizing the vibration. The present embodiment is configured as follows: A vibration plate 76, which is driven by a not-illustrated vibration generator, is provided between belt conveyors of a hand-baggage transportation bench 75 including two sheets of transportation belts 74. Moreover, using this vibration plate 76, the check target 57 as a whole is vibrated in an up-and-down direction 77, thereby, by this vibration, liberating the substances adhering to the surface of the check target 57. The absorption probe 8 in this case may be a mere cylinder.

(Seventh Embodiment)

According to the pick-up methods of directly absorbing the sample gas into the ion-source 20 by using the absorption probe 8 illustrated in FIG. 15 to FIG. 19, there exists the following problem: Namely, between the case where the detection is terminated with the high-speed screening mode alone and the skeptical case where the detection must be executed up to the detailed-checking mode, the times needed for the detection differ from each other. Consequently, when detecting the check target while displacing the check target by the hand-baggage transportation bench as is illustrated in FIG. 19, executing the following control is preferable by operating the transportation device of the hand-baggage transportation bench and the detection device thereof in a mutually-interconnected manner: Namely, at the time of the screening mode, the transportation is performed at a constant speed. Meanwhile, when performing the detection with several seconds spent thereon after the screening mode has been switched to the detailed-checking mode, the transportation speed is slowed down.

(Eighth Embodiment)

Also, according to the pick-up methods of directly absorbing the sample gas into the ion-source 20 by using the absorption probe 8 illustrated in FIG. 15 to FIG. 19, there exists the following problem: Namely, when absorbing, by the absorption probe 8, the sample gas picked up from the check target on the check bench transported at a constant speed, if the distance ranging from the absorption probe 8 to the mass spectrometer becomes long, it takes the absorbed sample gas a time to reach the ion-source 20 via the absorption hose 7. This condition lowers the detection speed, thereby causing a traffic congestion of the plural pieces of baggage on the check bench. Also, if the check target is a freight container, a vehicle, or the like which is located outdoors, the detection by the mass spectrometer cannot easily be performed.

Figure 20:
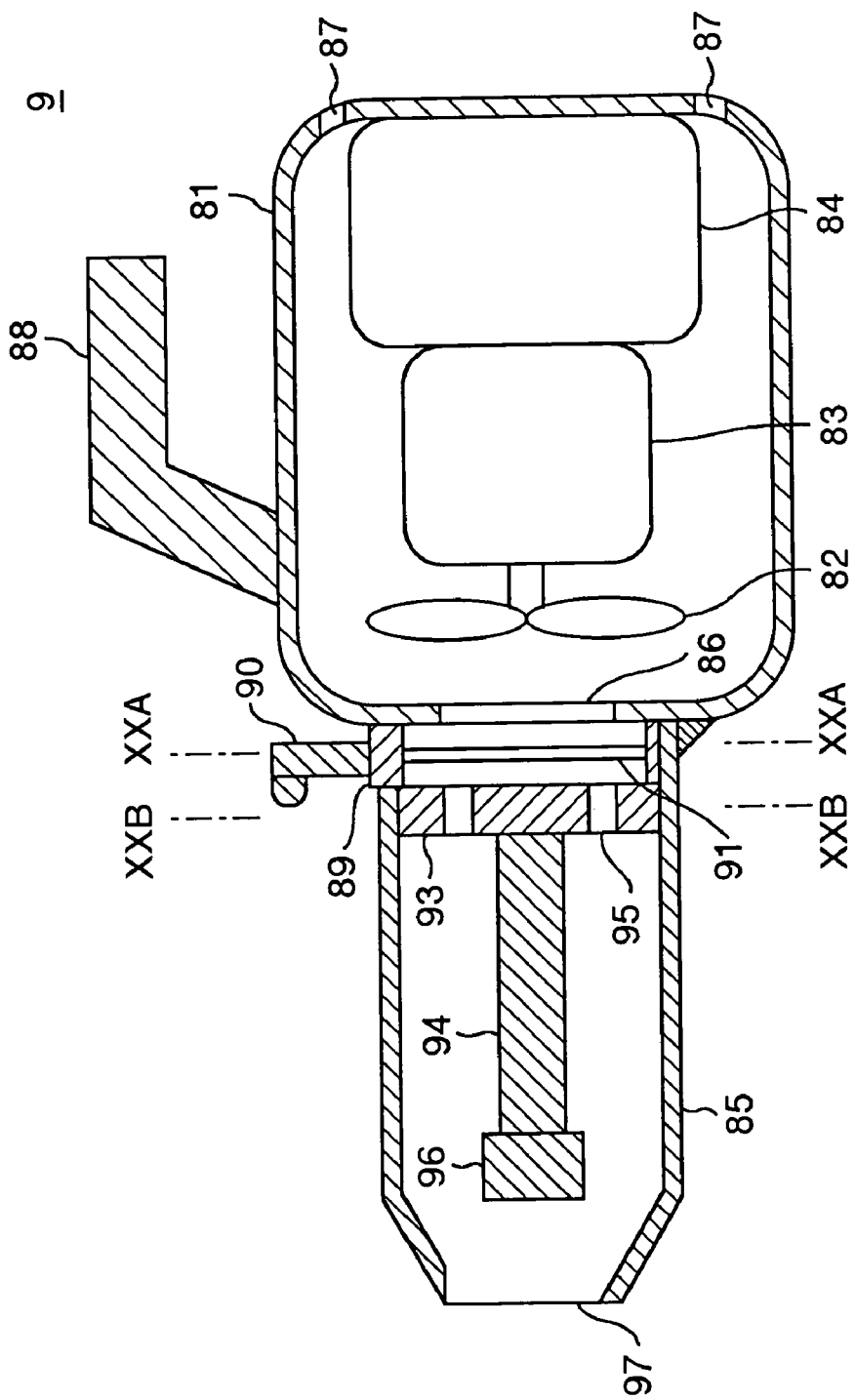
FIG. 20 is a diagram for illustrating an embodiment of a portable-type absorption probe according to the present invention.

FIG. 20 illustrates an embodiment of a portable-type absorption probe 9 which is preferable for the cases as described above. As is illustrated in the drawing, the portable-type absorption probe 9 is formed by including a case 81 and a cylinder-shaped absorption nozzle 85 mounted on a forward wall of the case 81. Here, the case 81 stores therein an absorption fan 82, a motor 83 for driving this fan 82, and a battery 84 as the power-supply. Moreover, an absorption opening 86 is provided in the forward wall of the case 81 on which the absorption nozzle 85 is mounted, and an exhaust opening 87 is provided in a backward wall of the case 81. Also, a handle 88 is provided on the upper portion of the case 81.

Figure 21A:
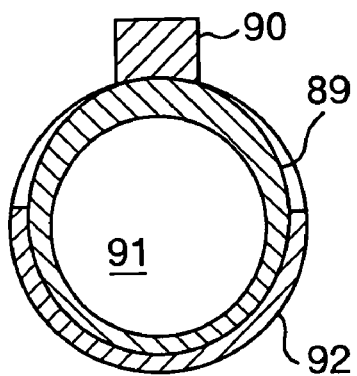
FIGS. 21A–21D are diagrams for illustrating the details of each unit of the embodiment in FIG. 20.
Figure 21B:
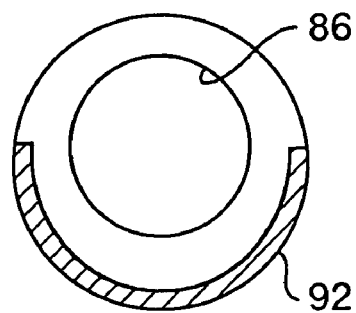
Figure 21C:
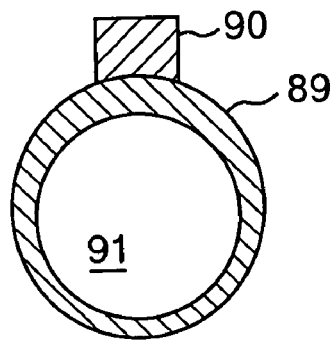

Meanwhile, a filter set-up unit for setting up a sample pick-up cassette filter 91 is provided on a connection unit between the absorption nozzle 85 and the case 81. As illustrated in FIG. 21C, the cassette filter 91 is configured to include a grasp unit 90 which is provided at a circumferential edge of a ring-shaped frame 89 of the filter 91. Here, an aperture circle positioned at the inner side of the frame 89 is formed in a manner of being decentered in a direction moving away from the grasp unit 90. The filter 91 is set up in such a manner that this aperture circle is filled. Various types of filter materials, such as a filter paper, can be used as the filter 91. In the filter set-up unit, as illustrated in FIG. 21B, a slit whose width is equal to the thickness of the cassette filter 91 is formed along a half circumference of the outer circumferential wall of the absorption nozzle 85. The cassette filter 91 is formed in an insertion/extraction-capable manner into/from this slit. As illustrated in FIG. 21A, the cassette filter 91 is held by a filter seat 92.

Figure 21D:
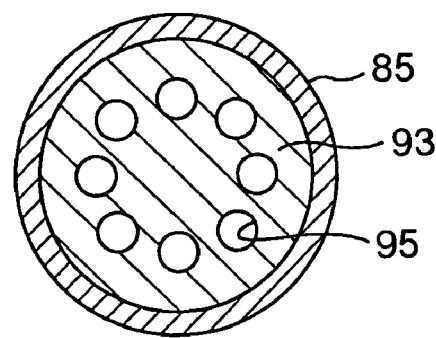

On the side closer to the front end of the absorption nozzle 85 than the filter set-up unit, a disc-shaped support board 93 is fixed on the inner wall of the absorption nozzle 85. A support rod 94 is provided by being extended from the central portion of the support board 93 toward the front-end direction of the absorption nozzle 85. Moreover, as illustrated in FIG. 21D, plural apertures 95 through which the sample gas flows are provided by being punched into the support board 93. Also, a heater 96, which is mounted at the front end of the support rod 94, is connected to the battery 84 via a not-illustrated switch. Also, the heater 96 is provided in a state of being positioned on a somewhat inner side than the front-end portion 97 of the absorption nozzle 85.

On account of this configuration, if the unused cassette filter 91 is inserted and set up into the filter set-up unit and if the heater 96 is switched ON and also the absorption fan 82 is rotated, the surrounding air is absorbed from the front-end portion of the absorption nozzle 85. At this time, if the front-end portion of the absorption nozzle 85 is brought closer to or brought into contact with the surface of a check target, the surface of the check target is heated by the heater 96. As a result, substances adhering to the surface of the check target are evaporated, then being absorbed together with the surrounding air. Next, the absorbed substances' vapors in the air are condensated at the filter 91, thereby being collected. Namely, if a special drug had adhered to the surface of the check target, the vapors can be collected by being condensated at the filter 91.

In this way, the cassette filter 91 on which the sample has been collected is set on the heater 5 illustrated in FIG. 5 or FIG. 14. This allows the detection of a special drug to be executed even if the mass spectrometer and the check target are set apart in space, or are set apart in time.

Here, just as the absorption probe 8 illustrated in FIG. 16A or FIG. 18, the portable-type absorption probe 9 in FIG. 20 can also be configured by combining the vibration generator, the vibrator, the optical fiber, and the like. Also, similarly, the absorption nozzle 85 can be configured as a double-layered cylinder where the air is injected from the inner cylinder so as to liberate adhering substances, and where the adhering substances are absorbed from the outer cylinder.

Also, in any one of the above-described embodiments, the explanation has been given concerning the example where the ion-trap mass spectrometer is applied as the mass spectrometer. However, it is needless to say that, when the present invention such as the absorption probe associated with the sample pick-up is applied to the embodiments, the mass spectrometer is not limited to the ion-trap mass spectrometer, but the conventional publicly-known mass spectrometers are applicable. For example, as is disclosed in JP-A-2001-093461, the mass spectrometer of the following so-called reverse-flow system is applicable: Namely, the introduction direction of a sample into a corona discharge region and the direction in which ions are extracted by the corona discharge are substantially opposed to each other, thereby enhancing the production efficiency of the ions.

As having been described so far, the special drug detection method and detection device of the present invention allow a sample pick-up to be easily performed from various types of check targets, and make it possible to shorten the pick-up time and the checking time.

Also, the special drug pick-up device of the present invention allows the sample pick-up to be easily performed from the various types of check targets, and makes it possible to shorten the pick-up time.

It should be further understood by those skilled in the art that although the foregoing description has been made on embodiments of the invention, the invention is not limited thereto and various changes and modifications may be made without departing from the spirit of the invention and the scope of the appended claims.

What is claimed is:

1. A special drug detection method, comprising:
   a step of applying a vibration to a check target,
   a step of absorbing, as a sample gas, the air on surface of or in proximity to said check target,
   a step of ionizing said absorbed sample gas,
   a first analysis step of analyzing masses of ions of said ionized sample gas thereby to acquire mass spectrums thereof, a first judgment step of judging whether or not ions having a first characteristic m/z value are present on the basis of said mass spectrums acquired at said first analysis step, a second analysis step of performing a tandem mass spectrometry in correspondence with a judgment result acquired at said first judgment step, and a second judgment step of judging whether or not ions having a second characteristic m/z value are present on the basis of mass spectrums acquired by said tandem mass spectrometry.

2. The special drug detection method according to claim 1, further comprising a step of outputting a judgment result in correspondence therewith, said judgment result being acquired at said second judgment step.

3. The special drug detection method according to claim 2, wherein said judgment-result outputting step is a notification step of issuing an alarm.

* * * * *